(12) United States Patent
Nawaz et al.

(10) Patent No.: US 8,941,826 B2
(45) Date of Patent: *Jan. 27, 2015

(54) THREE-DIMENSIONAL (3D) HYDRODYNAMIC FOCUSING USING A MICROFLUIDIC DEVICE

(75) Inventors: Ahmad Ahsan Nawaz, State College, PA (US); Xiaole Mao, Mason, OH (US); Tony Jun Huang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 349 days.

This patent is subject to a terminal disclaimer.

(21) Appl. No.: 13/362,983

(22) Filed: Jan. 31, 2012

(65) Prior Publication Data
US 2012/0196314 A1    Aug. 2, 2012

Related U.S. Application Data

(63) Continuation-in-part of application No. 12/207,699, filed on Sep. 10, 2008, now Pat. No. 8,120,770.

(60) Provisional application No. 60/971,054, filed on Sep. 10, 2007.

(51) Int. Cl.
*G01N 1/10* (2006.01)
*G01N 15/14* (2006.01)
(Continued)

(52) U.S. Cl.
CPC .......... *G01N 15/1404* (2013.01); *B01F 5/0647* (2013.01); *B01F 13/0062* (2013.01); *B01L 3/502776* (2013.01); *G01N 21/05* (2013.01); *G01N 21/6458* (2013.01); *B01L 2200/0636* (2013.01); *B01L 2300/0816* (2013.01); *B01L 2300/0861* (2013.01);
(Continued)

(58) Field of Classification Search
CPC ................ G01N 15/1404; G01N 2015/1413; G01N 21/05
USPC ..................... 356/246, 39; 250/428
See application file for complete search history.

(56) References Cited

U.S. PATENT DOCUMENTS 5,012,118 A * 4/1991 Preikschat et al. ........... 250/574
6,592,822 B1 * 7/2003 Chandler ................ 422/82.05
(Continued)

FOREIGN PATENT DOCUMENTS

WO    WO 85/05680    * 12/1985    ......... G01N 15/1436

OTHER PUBLICATIONS

Ambrose et al. (Single molecule fluorescence spectroscopy at ambient temperature) / Chem. Rev. 1999, 99, 2929-2956.*

(Continued)

*Primary Examiner* — Michael A Lyons
*Assistant Examiner* — Rufus Phillips
(74) *Attorney, Agent, or Firm* — Gifford, Krass, Sprinkle, Anderson & Citkowski, P.C.

(57) ABSTRACT

A microfluidic device comprises inlets for a sample flow and an out-of-plane focusing sheath flow, and a curved channel section configured to receive the sample flow and out-of-plane focusing sheath and to provide hydrodynamic focusing of the sample flow in an out-of-plane direction, the out-of-plane direction being normal to a plane including the curved channel. Examples of the invention also include improved flow cytometers.

20 Claims, 16 Drawing Sheets

(51) Int. Cl.
*B01F 5/06* (2006.01)
*B01F 13/00* (2006.01)
*B01L 3/00* (2006.01)
*G01N 21/05* (2006.01)
*G01N 21/64* (2006.01)
*G01N 21/03* (2006.01)

(52) U.S. Cl.
CPC . *B01L 2400/0409* (2013.01); *B01L 2400/0487* (2013.01); *B01L 2400/084* (2013.01); *G01N 2015/1413* (2013.01); *G01N 2021/0346* (2013.01); *G01N 2021/058* (2013.01); *G01N 2021/6482* (2013.01)
USPC .......................................................... 356/246

(56) References Cited

U.S. PATENT DOCUMENTS

| | | | |
|---|---|---|---|
| 7,423,751 B2 * | 9/2008 | Hairston et al. | 356/318 |
| 7,641,856 B2 * | 1/2010 | Padmanabhan et al. | 422/73 |
| 7,689,026 B2 * | 3/2010 | Fujii | 382/141 |
| 8,120,770 B2 * | 2/2012 | Huang et al. | 356/246 |
| 2004/0266022 A1 | 12/2004 | Sundararajan et al. | |
| 2007/0117086 A1 | 5/2007 | Evans et al. | |
| 2009/0014360 A1 | 1/2009 | Toner et al. | |
| 2009/0323061 A1 | 12/2009 | Novotny et al. | |

OTHER PUBLICATIONS

Mao, Xiaole, Waldeisen, John Robert, Huang, Tony Jun, "Microfluidic drifting"—implementing three-dimensional hydrodynamic focusing with a single-layer planar microfluidic device, Lab Chip, 2007, vol. 7, 1260-1262.
Shi, Jinjie, Mao, Xiaole, Ahmed, Daniel, Coletti, Ashley, Huang, Tony Jun, Focusing microparticles in a microfluidic channel with standing surface acoustic waves (SSAW), Lab Chip, 2008, vol. 8, 221-223.
Ottino, Julio M., Wiggins, Stephen, Introduction: mixing in microfluidics, Phil. Trans. R. Soc. Lond., 2004, 362, 923-935.
Chin, Curtis D., Linder, Vincent, Sia, Samuel K., Lab-on-a-chip devices for global health: Past studies and future opportunities, Lab Chip, 2007, vol. 7, 41-57.
Chaw, K.C., Manimaran, M., Tay, E.H., Swaminathan, S., Multi-step microfluidic device for studying cancer metastasis, Lab Chip, 2007, vol. 7, 1041-1047.
Simonnet, Claire, Groisman, Alex, Two-dimensional hydrodynamic focusing in a simple microfluidic device, Appl. Phys. Lett. 87, 114104 (2005).
Chang, Chih-Chang, Huang, Zhi-Xiong, Yang, Ruey-Jen, Three-dimensional hydrodynamic focusing in a two-layer polydimethylsiloxane (PDMS) microchannels, J. Micromech. Microeng. 17 (2007) 1479-1486.
Sundararajan, Narayan, Pio, Michael S., Lee, Luke P., Berlin, Andrew A., Three-Dimensional Hydrodynamic Focusing in Polydimethylsiloxane (PDMS) Microchannels, Journal of Microelectromechanical Systems, vol. 13, No. 4, Aug. 2004.
Sudarsan, Arjun P., Ugaz, Victor, M., Multivortex micromixing, PNAS, 2006, vol. 103, No. 19, 7228-7233.
Yang, Ren, Feeback, Daniel L., Wang, Wanjun, Microfabrication and test of a three-dimensional polymer hydro-focusing unit for flow cytometry applications, Sensors and Actuators A 118 (2005) 259-267.
Wolff, A., Perch-Nielsen, R., Larsen, U.D., Friis, P., Goranovic, G., Poulsen, C.R., Kutter, J.P., Telleman, P., Integrating advanced functionality in a microfabricated high-throughput fluorescent-activated cell sorter, Lab Chip, 2003, vol. 3, 22-27.
Mao, Xiaole, Waldeisen, John Robert, Juluri, Bala Krishna, Huang, Tony Jun, Hydrodynamically tunable optofluidic cylindrical microlens, Lab Chip, 2007, vol. 7, 1303-1308.
Howell, Peter B., Jr., Mott, David R., Golden, Joel P., Ligler, Frances S., Design and evaluation of a Dean vortex-based micromixer, Lab Chip, 2004, vol. 4, 663-669.
Sudarsan, Arjun P., Ugaz, Victor M., Fluid mixing in planar spiral microchannels, Lab Chip, 2006, vol. 6, 74-82.

* cited by examiner

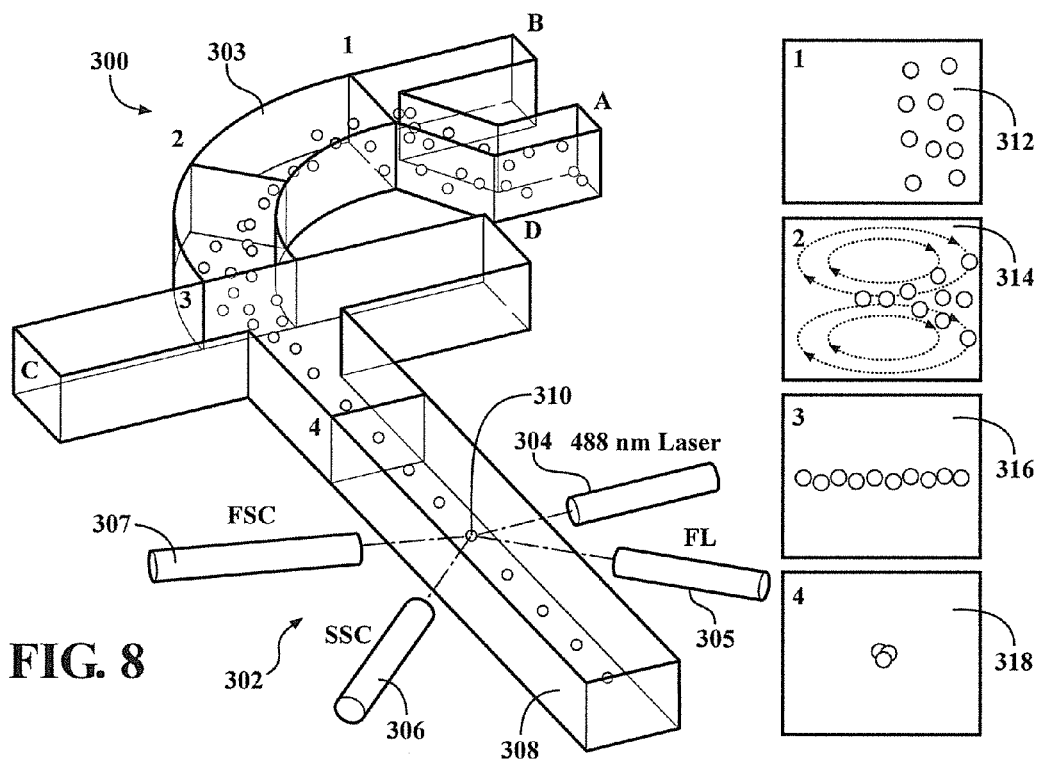
FIG. 8
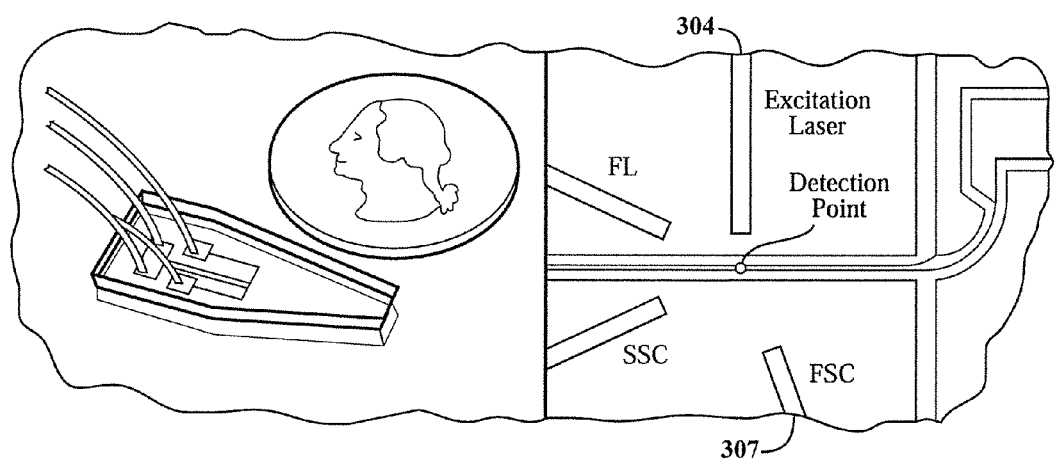
FIG. 9A  FIG. 9B

THREE-DIMENSIONAL (3D) HYDRODYNAMIC FOCUSING USING A MICROFLUIDIC DEVICE

REFERENCE TO RELATED APPLICATION

This application is a Continuation-in-Part of U.S. patent application Ser. No. 12/207,699, filed Sep. 10, 2008, which claims priority from U.S. provisional patent application Ser. No. 60/971,054, filed Sep. 10, 2007, the entire content of both of which are incorporated herein by reference.

GOVERNMENT SUPPORT

This invention was made with government support under Grant Nos. ECCS0609128 and ECCS0824183, awarded by the National Science Foundation and Grant No. OD007209, awarded by the National Institutes of Health. The government has certain rights in the invention.

FIELD OF THE INVENTION

The present invention relates to hydrodynamic focusing and applications thereof.

BACKGROUND OF THE INVENTION

Hydrodynamic focusing is used to compress a sample flow, typically in two dimensions. Improved methods of hydrodynamic focusing would be useful for numerous applications, such as flow cytometry and single molecule fluorescence.

SUMMARY OF THE INVENTION

Three dimensional (3D) hydrodynamic focusing was achieved in a microfluidic device. A sample flow and a vertical focusing sheath flow were passed through a curved channel section, allowing hydrodynamic focusing (i.e. flow compression) of the sample flow in a direction normal to the plane of the sample flow, which may be normal to a substrate. This process may be termed microfluidic drifting. A second horizontally focusing sheath flow can be used to achieve hydrodynamic focusing in the plane of sample flow, orthogonal to the first focus direction, for example in a direction parallel to a substrate. Hence, a combination of these effects permits 3D hydrodynamic focusing to be readily achieved, giving a sample flow narrowed (compressed) both horizontally and vertically. The compressed flow allows improved analyte detection, chemical processing, biochemical processing, flow cytometry, chemical processing and the like, in particular allowing more reliable single molecule sensitivity in some applications.

In representative examples, the sample flow, vertical focusing sheath flow, and horizontally focusing sheath flow are all substantially coplanar, and may be parallel to a planar substrate, allowing substantial simplification of device fabrication. For the first time, 3D hydrodynamic focusing was achieved without need for any out-of-plane flow, allowing planar devices to be fabricated using a 2D lithographic process. Analyte throughput in the detection region is increased, and the probability of detecting an analyte in the sample flow is increased. These advantages are useful in a wide range of applications.

Hydrodynamic focusing devices using microfluidic drifting may be used in many applications which would otherwise be impractical or less accurate using conventional microfluidic approaches. For the first time, 3D hydrodynamic focusing was achieved using a single-layer planar microfluidic device, which can be fabricated using 2D lithography.

An example microfluidic device comprises a generally planar substrate supporting a sample flow inlet configured to receive a sample flow, a first flow inlet configured to receive a first sheath flow (there may optionally be other sheath flows), and a curved channel. The curved channel is configured to receive the sample flow and the first sheath flow and to provide out-of-plane hydrodynamic focusing of the sample flow, the sample flow being compressed along a direction normal to the substrate. Example devices are single layer microfluidic devices, in which the sample flow, the first sheath flow, and any additional sheath flows are generally coplanar. For example, in-plane hydrodynamic focusing sheath flows may be used to provide hydrodynamic focusing of the sample flow along a direction parallel to the substrate, the first sheath flow and the in-plane hydrodynamic focusing sheath flows together providing three-dimensional hydrodynamic focusing of the sample flow.

An example apparatus may include an output channel, the three-dimensional hydrodynamic focusing acting to compress the sample flow within a region near the center of the output channel, surrounded by the sheath flows. A radiation detector may be configured to detect radiation from the sample flow, and an excitation source may be configured to induce the radiation within the sample flow. Examples of the present invention include methods and apparatus for fluorescence detection of molecules and/or other fluorophors, including single-molecule fluorescence. Example apparatus include a flow cytometer, a fluorescence spectrometer, a laser spectrometer, a laminar mixer, a reaction vessel, or a chemical processing device, and may be multi-functional devices having one or more of such functions, and/or other functions.

A curved channel may have an inner side wall and an outer side wall, the side walls being generally normal to the substrate, the sample flow inlet and the first flow inlet being configured to introduced the sample flow and first sheath flow into the curved channel to initially have a fluid interface that is generally parallel to the side walls. As the sample flow and sheath flow progress through the curved channel, the fluid interface between them becomes highly curved, and the sample flow may the curved channel as a thin layer, narrowed in a direction normal to the substrate and extending across the width of the curved channel at the exit thereof. The sample flow may be introduced to the curved channel so as to be initially closer to the inner side wall, for example between the fluid interface with the first sheath flow and the inner side wall.

A method of hydrofluidic focusing a sample flow in a planar microfluidic device having a planar substrate comprises passing the sample flow and a sheath flow through a curved channel disposed on the planar substrate, the curved channel section providing hydrofluidic focusing of the sample flow in a direction generally normal to the planar substrate. The sample flow may be further passed through a linear channel section between a pair of in-plane focusing sheath flows, so as to obtain three-dimensional hydrofluidic focusing of the sample flow. The sample flow including biological cells, the method being a method of flow cytometry. The sample flow may include fluorescent molecules, the method being a method of single-molecule fluorescence spectroscopy. Other analytical methods may be improved by examples of the present invention.

An example apparatus is a planar microfluidic flow cytometer, including a particle focusing stage and a particle characterization stage. The particle focusing stage includes a substrate, a sample flow inlet receiving a sample flow, a first flow inlet receiving a first sheath flow, and a curved channel, the curved channel configured to receive the sample flow and the first sheath flow. The curved channel has a bend angle, and is configured to provide out-of-plane hydrodynamic focusing of the sample flow when the sample flow and first sheath flow pass together through the curved channel. The sample flow inlet, the first flow inlet, and the curved channel are supported by the substrate, with the curved channel being generally parallel to the substrate so that the sample flow is compressed along a direction normal to the substrate.

In some examples, the bend angle is greater than 90 degrees, in particular greater than or equal to 135 degrees. In some examples, the bend angle is approximately 180 degrees, and in some examples the bend angle is between 135 degrees and 225 degrees.

Example apparatus include a microfluidic device configured to provide three-dimensional hydrodynamic focusing within an output channel, with optical access provided at the output channel. The optical access may include an optical path between an excitation source and an excitation point within the output channel. The optical path may include one or more optical fibers. Similarly, an optical path may be provided to collect radiation, including one or more optical fibers. An optical path may include a window to the output channel.

An example device has one or more inlets for in-plane hydrodynamic focusing sheath flows, the in-plane hydrodynamic focusing sheath flows providing hydrodynamic focusing of the sample flow along a direction parallel to the substrate and an output channel, the first sheath flow together with the in-plane hydrodynamic focusing sheath flows providing three-dimensional hydrodynamic focusing of the sample flow within the output channel. The sample flow, the first sheath flow, and the in-plane hydrodynamic focusing sheath flows may be co-planar.

Example apparatus may further include a laser configured to excite the sample flow at an excitation point within the output channel, which may be the point of narrowest particle flow (or smallest particle focus diameter). A radiation detector may be configured to receive radiation from the sample flow. The radiation may be induced by the laser, and may include fluorescence and/or scattered laser radiation.

One or more optical fibers may be configured to convey radiation from the laser (or other excitation source) to excitation point, and/or to collect radiation from the excitation point. In some examples, the apparatus may be a single-layer planar microfluidic flow cytometer with integrated optical fibers allowing optical paths to the excitation point.

A method of characterizing particles includes hydrofluidic focusing a sample flow in a planar microfluidic device, the sample flow being a fluidic suspension of particles, for example by passing the sample flow and a sheath flow through a curved channel section disposed on the planar substrate, the curved channel section providing hydrofluidic focusing of the sample flow in a direction generally normal to the planar substrate. The sample flow may then be passed through a linear channel section between a pair of in-plane focusing sheath flows to obtain three-dimensional hydrofluidic focusing of the sample flow within an output channel. The sample flow, the sheath flow, and the pair of in-plane focusing sheath flows may be generally coplanar. The particles may then characterized within the output channel by optical, electrical, magnetic, ultrasound, or other techniques or combinations thereof.

A sample flow may include biological cells, the method including hydrodynamic focusing of the biological cells within the sample flow to allow characterization of the biological cells. A sample flow may include labeled particles, such as fluorescent-labeled cells or molecules. Hydrodynamic focusing of fluorescent particles, molecules, cells, or other biological materials facilitates detection using single-molecule fluorescence spectroscopy.

In some examples, a further particle sorting stage is used to sort the characterized particles into a selected output channel of a plurality of output channels.

BRIEF DESCRIPTION OF THE DRAWINGS

FIG. 2A shows a photomask used, FIG. 2B shows details of the hydrodynamic focusing section, and FIG. 2C shows a schematic of an optical setup for side-view epifluorescence imaging of the focused flow;

FIG. 3A is a top view of the sample flow pattern during the 3D focusing process, FIG. 3B is a CFD simulation under the same flow conditions, FIG. 3C is a side view of the 3D focused sample flow (flow direction: right to left) in the main channel, and FIG. 3D is the same view of the channel after the flow is stopped;

FIG. 8 shows the configuration of an example flow cytometry chip.

FIGS. 9A and 9B show images of an assembled flow cytometry chip, FIG. 9A shows the size is comparable to a U.S. quarter, the device including a fluidic channel, optical fibers, and coupled laser beam, and FIG. 9B is microscopic image indicating hydrodynamic focusing and the arrangement of the optical fibers, with inlet A mixed with fluorescent dye to show the focused stream.

DETAILED DESCRIPTION OF THE INVENTION

Figure 1:
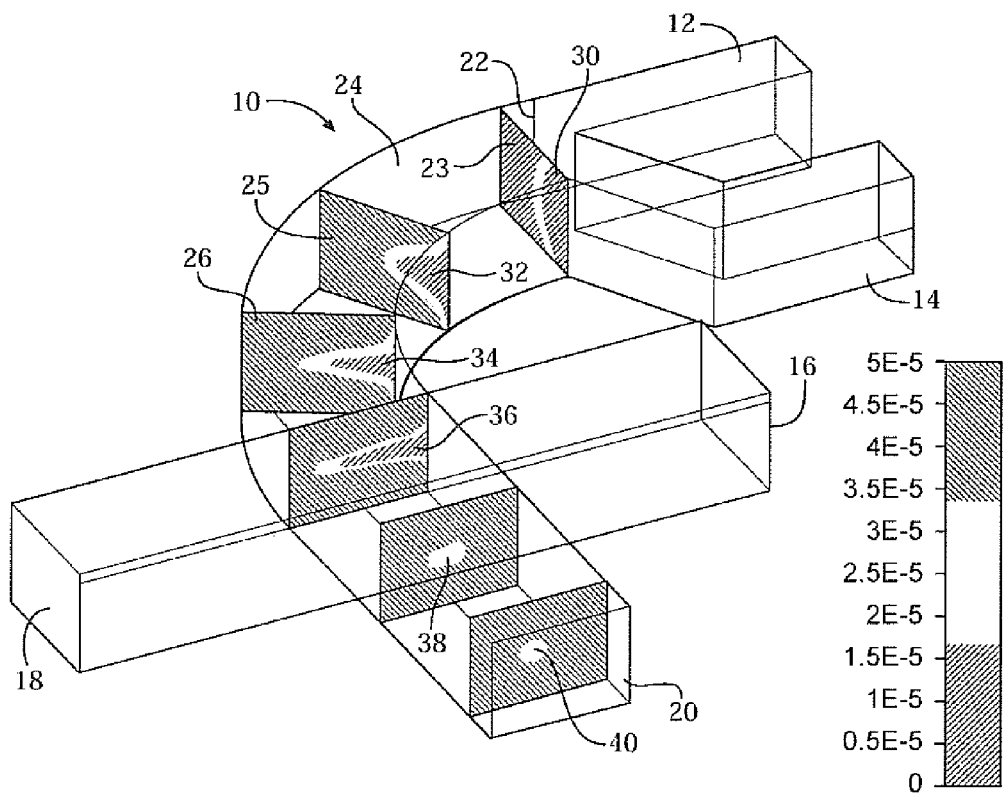
FIG. 1 is a schematic of a 3D hydrodynamic focusing process achieved using a "microfluidic drifting" technique, in which slices 1-10 are the cross-sectional profiles of the fluorescein dye concentration in the focusing device.

Hydrodynamic focusing can be used to compress a sample flow, typically in two dimensions. The focusing process can be used to increase sample throughput in the detection region, assisting characterization of the sample flow. In a conventional planar device, spreading of the sample flow in a vertical direction (here, the term vertical refers to a direction perpendicular to the plane of the sample flow) reduces characterization efficiency. In some applications, an analyte can be missed, particularly for flow cytometry and single molecule analysis methods. Improved techniques are required to give three dimensional (3D) hydrodynamic focusing.

A novel fluid manipulation technique termed "microfluidic drifting" was developed which allows 3D hydrodynamic focusing. A single-layer planar microfluidic device was fabricated that provided effective and robust 3D hydrodynamic focusing, without the need for any extensive fabrication technique other than standard soft lithography. A "microfluidic drifting" technique can be effectively used in focusing small molecules and also larger microparticles such as biological cells. "Microfluidic drifting" is readily applicable for 3D hydrodynamic focusing of biological cells for microfluidics based flow cytometry devices. Particles may include cells, other biological structures, macromolecules, or other suspended materials within a fluid medium, more particularly a liquid supporting medium.

Embodiments of the present invention include apparatus and methods for hydrodynamic focusing. In some examples, microfluidic drifting based 3D hydrodynamic focusing comprises two steps. A sample flow can be focused in a first direction using the transverse Dean flow, and the sample flow can be focused in a second direction in horizontal plane using a sheath flow. The second direction may be parallel to a substrate plane, and in some examples may be referred to as the horizontal direction. The first direction may be normal to the substrate, and may be referred to as the vertical direction.

An example microfluidic device, operable to provide three-dimensional hydrodynamic focusing of a sample flow, includes a curved channel section operable to provide hydrodynamic focusing in an out-of-plane direction, relative to a plane including the curved channel. An in-plane sheath flow can then provide in-plane focusing, the combination of focusing effects cooperatively focusing the sample flow. The 3D focused sample flow is compressed, both in out of plane and in plane directions, relative to the incoming sample flow. Focusing in one or both planes may be selectively switched on or off as required, for example for use with different analytical techniques. For some applications, only out-of-plane focusing may be used, for example using a vertical focusing sheath flow and curved channel to compress the sample flow into a narrow horizontal band parallel to the substrate. A radiation beam may then be passed through the horizontal band, or other analytical technique used.

Planar microfluidic devices according to embodiments of the present invention may be used in various applications, such as a flow cytometer, single molecule detection based analysis, fluorescence spectrometer, other laser spectrometer, laminar mixer, micro-chemical reaction vessel, chemical or biochemical kinetics measuring device, or other analytical instrument or chemical processing device. Applications include controlled reaction vessels capable of controllably reacting individual molecules.

A curved channel can be used to provide out-of-plane focusing of the sample flow, by co-injection of a sample flow and a vertical focusing sheath flow into the curved channel. The sample flow and a vertical focusing sheath flow, have, for example, different densities. In examples described below, the curved channel section has a bend angle of 90 degrees. However, this example is not limiting and different bend angles may be used, for example in the range 10-180 degrees. The curved channel may be generally in a plane parallel to a supporting substrate, so that the focusing effect is generally out of the plane of the substrate. In some examples, the substrate may be flexible and/or curved, allowing other hydrodynamic effects to be obtained if desired.

An improved method of three-dimensional hydrofluidic focusing of a sample flow includes passing the sample flow through a curved channel along with a second flow of a different density, and further passing the sample flow through a fluid sheath crossing the sample flow, the curved channel and fluid sheath cooperatively providing three-dimensional hydrofluidic focusing of the sample flow.

An example microfluidic device includes a sample flow and a first sheath flow injected into a microfluidic channel. The adjacent injection of the flows into the channel initially results in an optically smooth, nearly vertical interface, due to the laminar flow that typically dominates in microfluidic channels. However, on entering a curved channel, the fluids experiences centrifugal force along the curved trajectory. Any fluid flowing in the middle of the channel (where the flow velocity is the highest) experiences a higher centrifugal force than the surrounding flow. As a result, a pair of secondary counter-rotating vortices (Dean vortices) located in the upper and lower half of the cross-sectional plane of the channel is induced, and the secondary vertical flow perturbs the fluidic interface. Fluid in the middle of channel is directed towards the outer channel wall, and fluid at the top and bottom of the channel is directed towards the inner channel wall. Consequently, an originally vertical fluidic interface bows outward, creating a curved interface. The magnitude of the centrifugal effect and consequent bowing of the interface is related to the ratio of inertial and centrifugal force to viscous force. The shape of the fluidic interface can be readily adjusted by changing the flow rate, so as to obtain a substantially vertically focused flow, the sample flow extending over most of the width of the curved channel, but focused in the center in the vertical direction. Once the fluids exit the 90-degree curve, the fluidic interface profile may be approximately static, before any significant distortion caused by diffusion and/or gravity. A horizontal sheathing flow can then used to obtain a fluid flow further focused in the horizontal plane, so that the sample flow is focused vertical and horizontally. In some examples of the present invention, horizontal focusing is optional, and may not be present.

FIG. 1 shows an example device for 3D focusing, the focusing mechanism being shown using a computational fluid dynamic (CFD) simulation (CFDACE+, ESI-CFD, Huntsville, Ala.). The figure shows an apparatus 10 with sample flow inlet 14, first sheath flow (vertical focusing sheath flow) inlet 12, curved channel 24, first horizontal focusing sheath flow inlet 16, second horizontal focusing sheath flow inlet 18, and flow outlet 20 (which may be part of an output channel). The example device shown includes four inlets for sample and sheath flows, one outlet, and a curved channel with a 90-degree bend angle, in this example having a mean radius of 250 µm. The widths of channels for the sample flow and the vertical focusing sheath flow are 50 µm and the two side channels for horizontal focusing sheath flows are 100 µm wide. The width of the main channel (measured parallel to the substrate normal to the side walls) is 100 µm and the channel depth (measured normal to the substrate) throughout the entire device is 75 µm. Dimensions are exemplary, and other radii, bend angles, and/or channel dimensions may be used. The inlets and channels may be formed in any appropriate material, and may be supported by a planar substrate (not shown in FIG. 1 for illustrative clarity).

The 3D hydrodynamic focusing is accomplished in a two-step sequence. The first step focuses the sample flow in the vertical direction by using what may be termed a "microfluidic drifting" technique. This term refers to the lateral drift of the sample flow caused by the secondary flow (possibly through the action of Dean Vortices) induced by the centrifugal effect in the curve of microfluidic curved channel.

In FIG. 1, the sample flow (50 µM fluorescein dye solution, slice 1), and the vertical focusing sheath flow (water, slice 2) are co-infused into the 90-degree curve of the curved channel 24. The shading and bargraph represents fluorescein molar concentration. At the join 22 of the first sheath flow and sample flow, the flows are adjacent within the channel, and the boundary between the flows is vertical. In this context, the term vertical refers to the normal to the substrate and is used for convenience. However, use of this term is not intended to limit the orientation of the substrate. The figure shows a number of slices representing model flow configurations at that point, such as slice at 23 just within the curved channel 24. In the curved channel, the induced secondary flow causes the sample flow to drift laterally to the opposite side of channel (slices 5-8). The flow boundary becomes curved, with the flow profile showing the sample flow bulging into the sheath flow near the center of the flow channel, as shown at 30, 32, 34, and 36.

The final profile 36 of the drifted sample flow at the exit of the curved channel ("curve") is determined by the total flow rate through the curve as well as the flow rate ratio between the sample flow and vertical focusing sheath flow. By carefully controlling the total flow rate and flow rate ratio, the sample flow can be vertically focused into a thin horizontal flow sandwiched between the split vertical focusing sheath flows (at 36, slice 8). Focusing in the horizontal direction (slices 8-10) is conducted with two horizontal focusing sheath flows (water, slices 3 and 4) from inlets 16 and 18, which further compress the vertically focused sample flow from both sides. The combined effects of these two focusing steps result in a 3D hydrodynamically focused sample flow in the center of the microfluidic channel, shown at 38 and 40. The compression ratios for both the vertical and horizontal focusing can be readily altered by changing the flow rates of the sample flow and sheath flows.

Figure 2A:
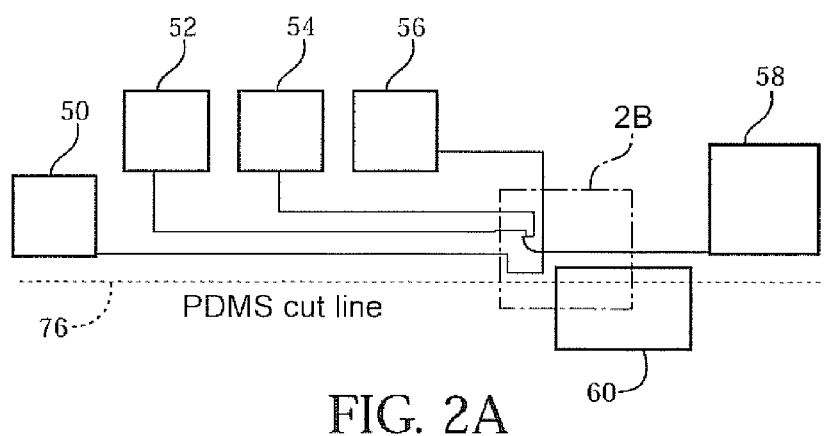
FIGS. 2A-2C illustrate a microfluidic device configuration for creating and characterizing a 3D focused flow, where
Figure 2B:
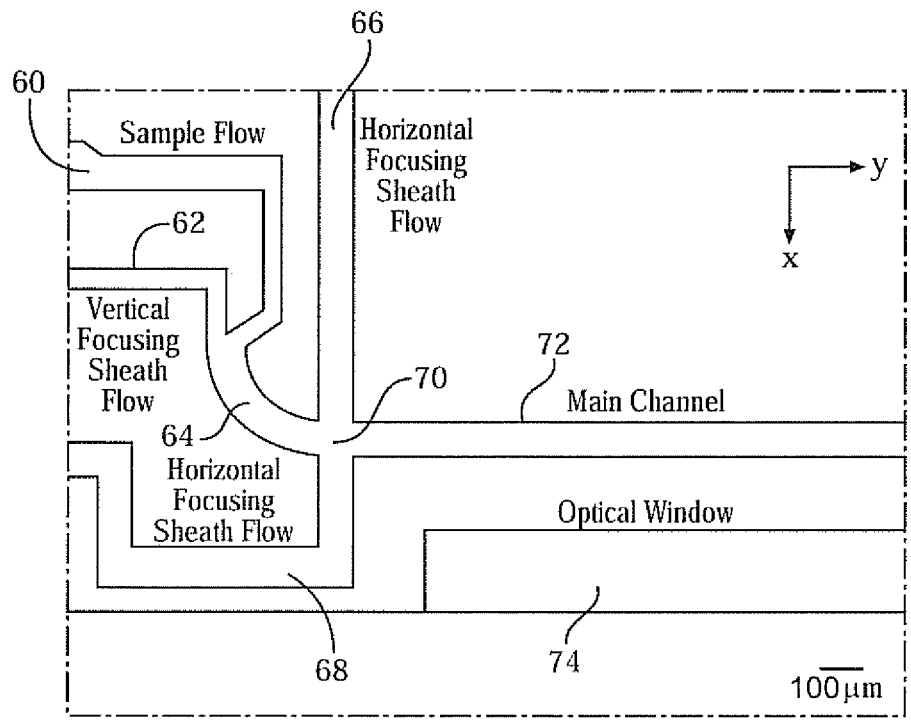
Figure 2C:
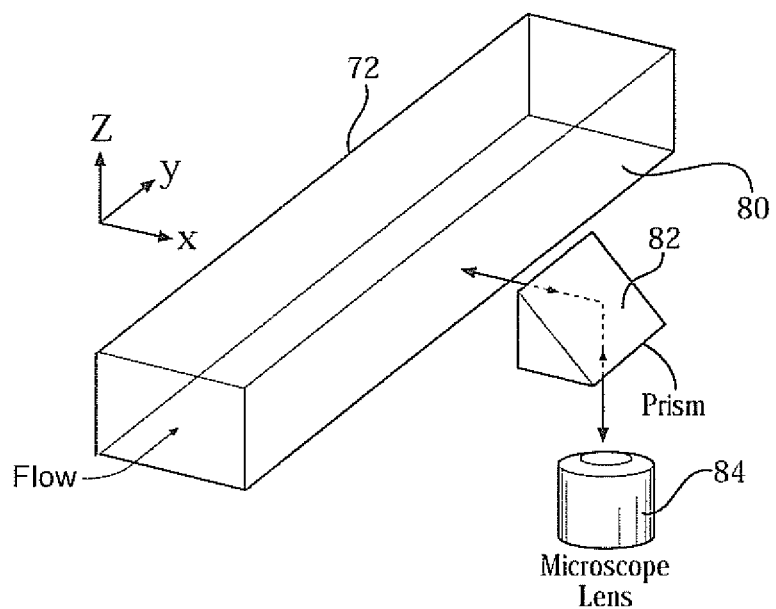

FIGS. 2A-2C show an example device design and optical setup for creating and characterizing a 3D focused flow. FIG. 2A shows the device having a sample flow inlet 54, vertical focusing sheath flow inlet 52, horizontal focusing sheath flow inlets 50 and 56, and outlet 58, and optical window 60. FIG. 2B shows a magnified detail of the hydrodynamic focusing portion, with sample flow channel 60, vertical focusing sheath flow channel 62, horizontal focusing sheath flow channels 66 and 68, and main channel 72. The main channel 72 is a portion of the output channel, which may be generally linear, in which hydrodynamic focusing is realized. An optical window 74, cut from window 60 as described below, allows visual access to the main channel 72.

The microfluidic channel was made by casting the PDMS on a planar silicon mold fabricated using the standard photolithography and deep reactive ion etching (DRIE). To observe the focusing in the vertical direction, a smooth, transparent optical window was placed adjacent to the main channel to allow side-view imaging of the focused flow. The PDMS substrate was cut along the "PDMS cut line" (dashed line 76 in FIG. 2A) to expose the optical window 74 to a light source (window 74 in FIG. 2B being formed from window 60 in FIG. 2A).

A 45-degree prism was placed adjacent to the optical window to deflect the excitation light and emission light so the side-view profile of the focused flow can be monitored using an epifluorescence microscope. FIG. 2C is a simplified schematic, showing part of the main channel 72 with side wall 80 visually accessible using prism 82 and microscope lens 84, the window not being shown for illustrative simplicity.

Experimentation of 3D hydrodynamic focusing was conducted as determined by the prior CFD simulations and visual evidence of 3D hydrodynamic focusing (both top-view and side-view) were obtained via epifluorescence microscopy. The fluorescein (50 µM) dyed sample flow and vertical focusing sheath flow (DI water) were co-infused into the 90-degree curve at flow rates of 50 µl/min and 337 µl/min, respectively. The horizontal focusing sheath flows (DI water) were injected from both sides at a flow rate of 225 µl/min.

Figure 3A:
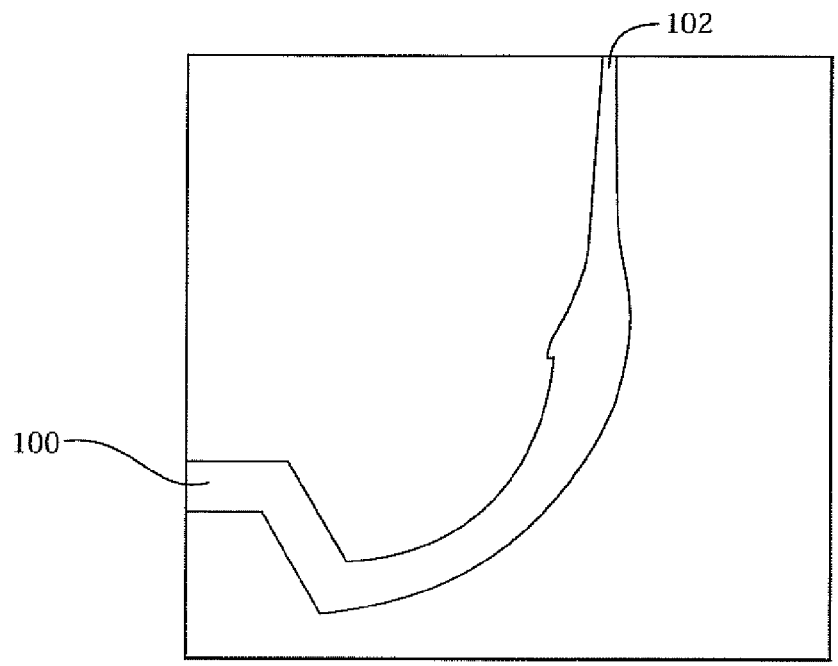
FIGS. 3A-3D illustrate sample flow patters, where

FIG. 3A depicts the top view of the fluorescent sample flow during the focusing process. The sample flow is fluorescent and shows up as the light-colored flow in this image, entering at 100 and exiting at 102. Once entering the 90-degree curve, the sample flow starts to drift to the opposite side of the channel, visually evident by the increase in the width of the sample flow. The width of the sample flow reaches its maximum at the exit of the 90-degree curve, upon which the flow is compressed by the horizontal focusing sheath flows to a horizontally focused flow at 102.

In sheath flow focusing, a central sample solution with a low flow rate flows within an outer fluid sheath traveling at a higher flow rate, thus enabling the compression of the inner sample flow. For example, both horizontally focusing sheath flows may enter the main channel at a higher speed than the sample flow.

Figure 3B:
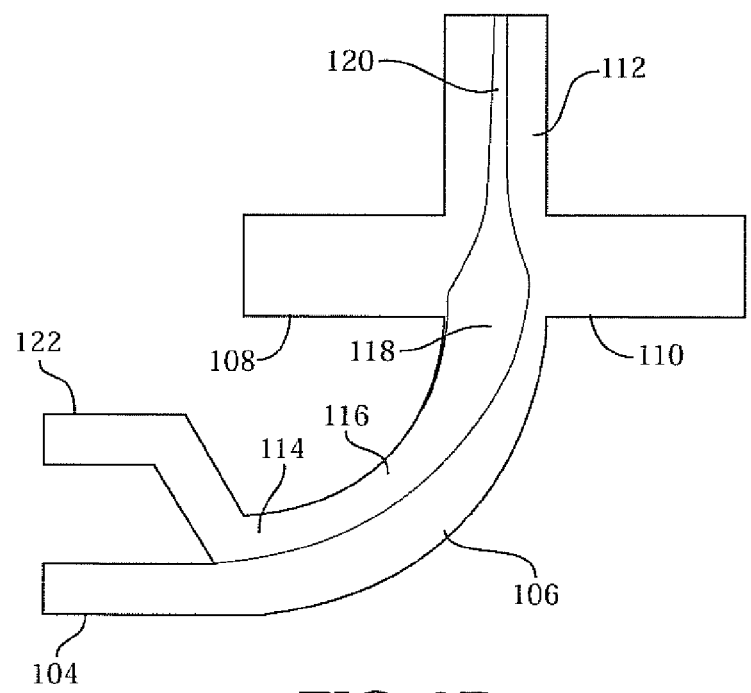

FIG. 3B shows a CFD simulation performed under conditions corresponding to the experimental conditions of FIG. 3A, which accurately replicated experimental observation. The figure shows sample flow 100, sheath flows 104, 108, and 110, and output flow 120. The sample flow is focused in the vertical direction (out of the plane of the figure) within the curved channel 106. The sample flow is widest in the horizontal direction as it exits the curved channel 106 and combines with the horizontal focusing sheath flows 108 and 110. The horizontal focusing narrows the simulated fluorescent region to 3D focused flow at 102.

Figure 3C:
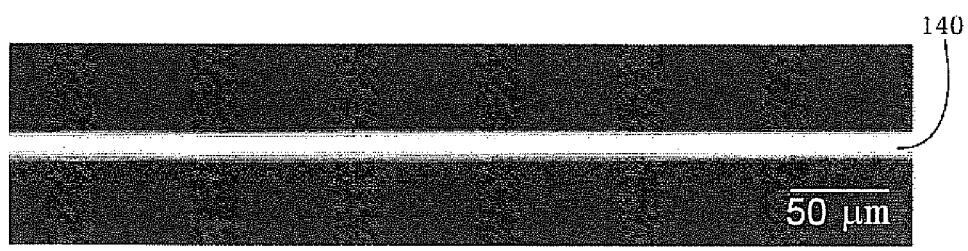

FIG. 3C depicts the side-view of the 3D focused flow 140 in the main channel. The sample flow is found to be focused in the center of channel with a total height of less than 15 µm.

Figure 3D:
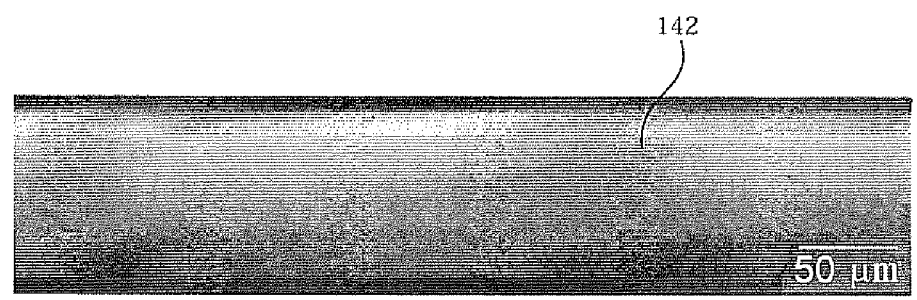

FIG. 3D shows the side-view of the main channel after the flows have been stopped. The fluorescent dye diffuses through the entire channel resulting in a uniform distribution of fluorescent dye at a much lower concentration. It was also observed that switching between static flow and 3D focusing takes less than 3 seconds and is highly repeatable Confocal microscopy was conducted in order to reveal the full 3D architecture of the sample flow in the 3D hydrodynamic focusing process. The 3D structure of the sample flow is constructed using a Z-stacked series of fluorescent images scanned at 2 µm intervals.

Figure 4A:
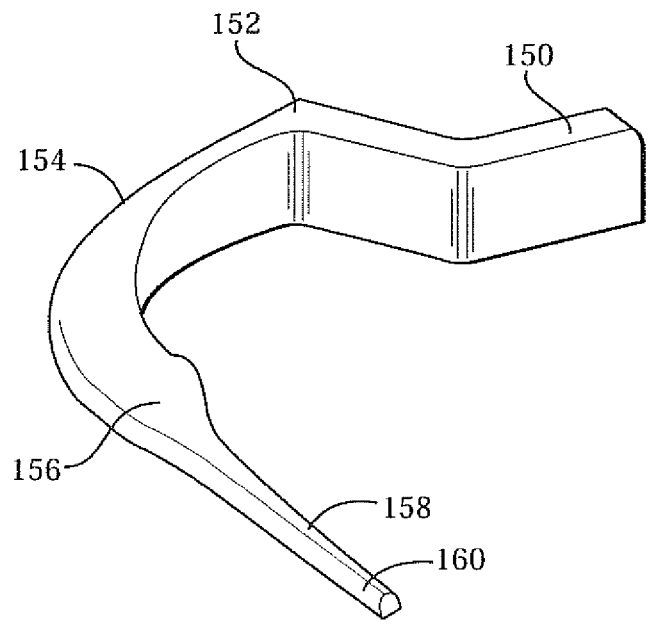
FIG. 4A shows the 3D architecture of the sample flow during the focusing process characterized by confocal microscopy.

FIG. 4A depicts the 3D image of the sample flow and clearly reveals the microfluidic drifting in the curve as well as the final 3D focused flow. The microscopy stacked image shows input sample flow at 150, joining with the vertical focusing sheath flow at 150 (the sheath flows are not fluorescent and hence do not show here), the sample flow interface with the sheath flow bending outwards within the curved channel 154. The sample flow is then focused horizontally by horizontal focusing sheathing flows incident at 156, the focusing occurring at 158 to form a narrower centralized sample flow at 160.

Figure 4B:
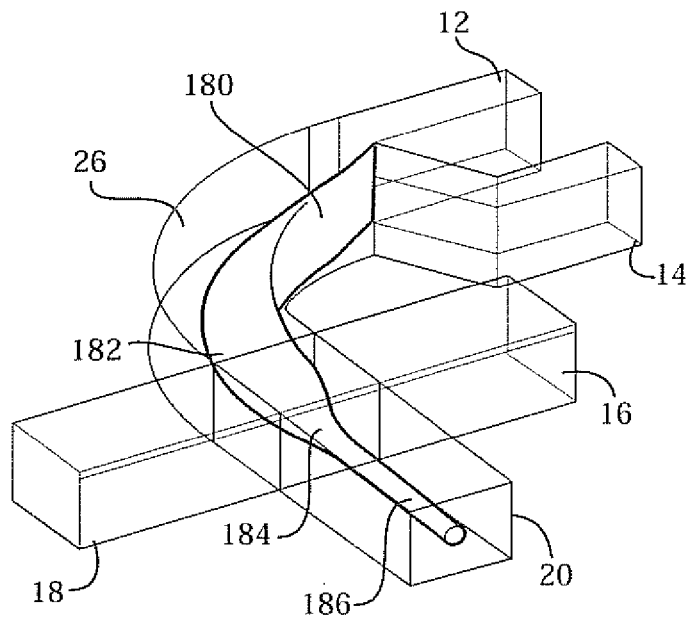
FIG. 4B shows the CFD simulation performed under the same flow conditions (an isosurface of fluorescein concentration 15 μM is arbitrarily chosen as the boundary of the sample flow)

FIG. 4B is a CFD simulation obtained with the same flow conditions. The CFD simulation was conducted using a finite-volume based commercial package, CFD-ACE+ (ESI-CFD, Huntsville, Ala.). The built-in flow module and chemistry module were used to simulate the flow and the fluorescent dye (fluorescein) distribution inside a three-dimensional (3D) focusing device. A computational grid was created using the ESI-GEOM tool of the ESI-CFD package. The grid has dimensions identical to the actual device except that only a portion of the device was modeled to reduce the computation load. The grid contains 123,000 computational cells to ensure sufficient grid density for the simulation. Strong agreement was observed between the confocal microscopic image and the simulated result.

The figure shows sample flow input 14, sheathing flow inputs 12, 16, 18, and 20, and output flow channel 20, as described in relation to FIG. 1. Initially, the sample flow and sheath flow are side by side in the channel with an approximately vertical interface, as shown at 180, but as they flow around the curved channel, the sample flow tends to locate at mid-height within the channel, with the sheathing flow moving to upper and lower regions of the sample flow. At the end of the curved channel 24, the flow profile 182 can be approximated by a sample flow between horizontal interfaces with sheathing flow above and below the sample flow. The horizontally focusing sheathing flows then tend to centralize the sample flow within the channel, as shown at 184 and 186.

Particle Focusing

Small molecules (for examples, molecules on the size on the order of a few nanometers or less) can follow the sample flow streamlines and can thus be effectively focused in applications such as single molecule detection. For larger particles such as biological cells (with a diameter of several micrometers), whose density is different from that of carrier fluids, tend to deviate from the streamlines, thus may cause adverse effect to 3D hydrodynamic focusing "microfluidic drifting". Numerical simulation and experimental validation were used to show that microfluidic drifting based 3D hydrodynamic focusing can effectively focus microparticles (including particles with size and density close to those of biological cells).

A numerical simulation of microparticle focusing process using a finite-volume (FV) based multi-physics package, ESI-CFD+ (ESI-CFD. The "flow module" and "spray module" were employed to simulate the motion of discrete particles in 3D focusing process.

Figure 5:
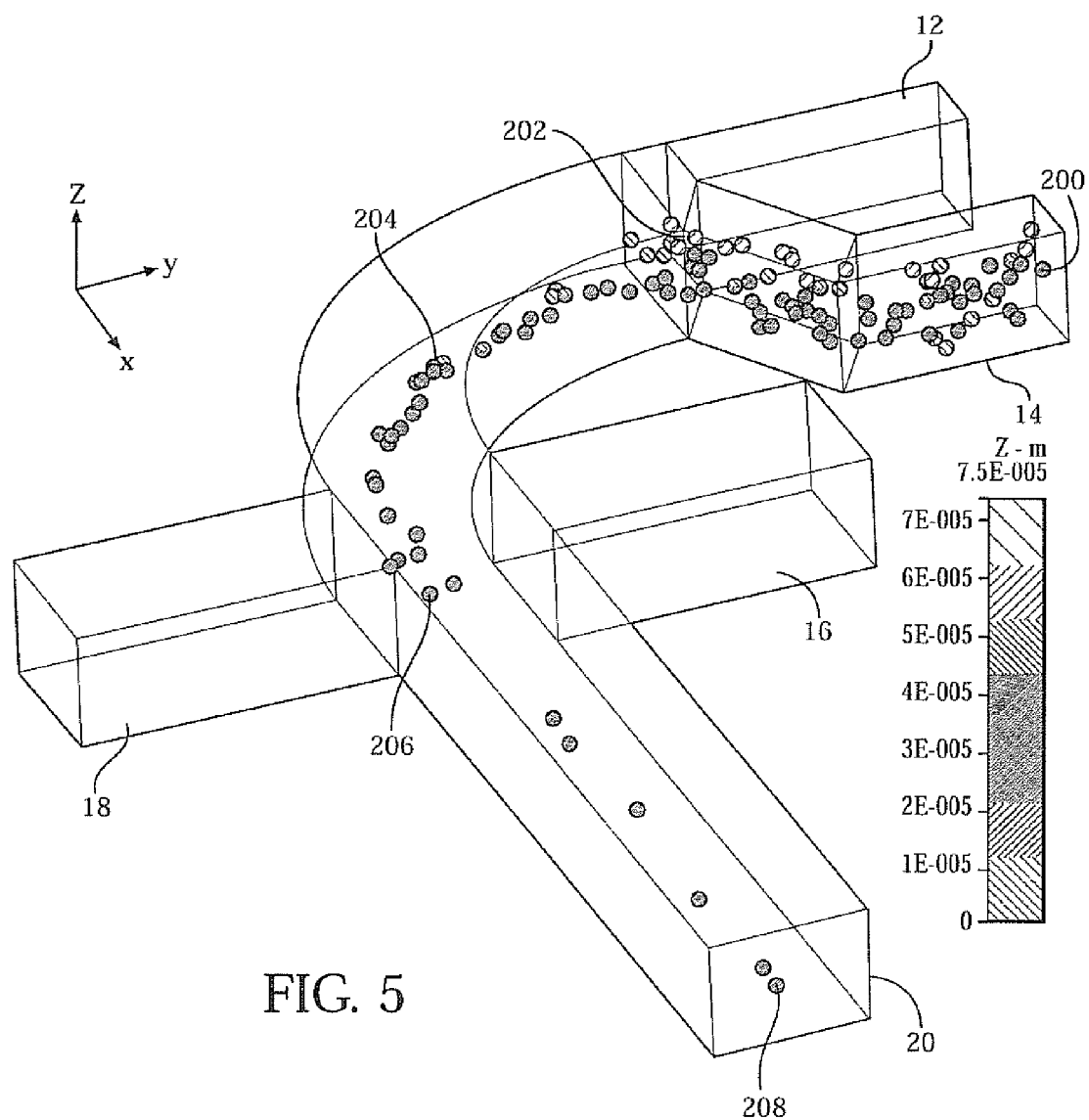
FIG. 5 illustrates hydrodynamic focusing of a sample flow comprising particles.

FIG. 5 shows a CFD simulation of 3D particle focusing process, indicating the height of individual particles. Particle sources were uniformly distributed in height at the particle inlet. The particles are shaded according to their height (Z direction, normal to the substrate). In X-Y plane, it is clearly shown that particles are lined up in the main channel. The height distribution of the particles change to approximately uniform height upon completion of 3D hydrodynamic focusing, indicating the particles are focused vertically to the center plane of the channel.

The sample flow input 14, sheathing flow inputs 12, 16, 18, and 20, and output flow channel 20 are as described in relation to FIG. 1. In this example, the input sample flow comprises particles such as 200. The vertical distribution of particles in the input flow is initially approximately random. The sample flow joins with the vertical focusing sheath flow at 202, and the drifting effect causes the particle height distribution to peak within the midpoint of the channel height. The horizontal focusing sheathing flows then centralizes the particles as shown at 208. This effect is analogous to that observed with the fluorescent sample flow discussed above.

The 3D particle focusing process was experimentally characterized with fluorescent polystyrene microparticles with size (diameter=7 and density ($1.05 \times 103$ kg/m$^3$), similar to biological cells.

Figure 6A:
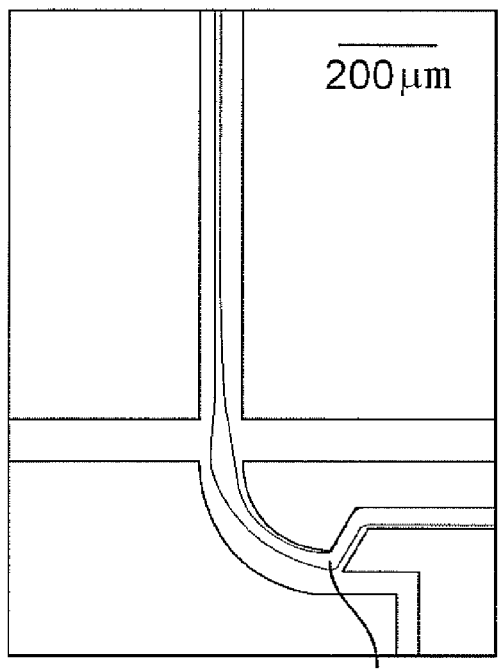
FIGS. 6A-6B are representations of fluorescent and bright field images (respectively) of 3D particle focusing.
Figure 6B:
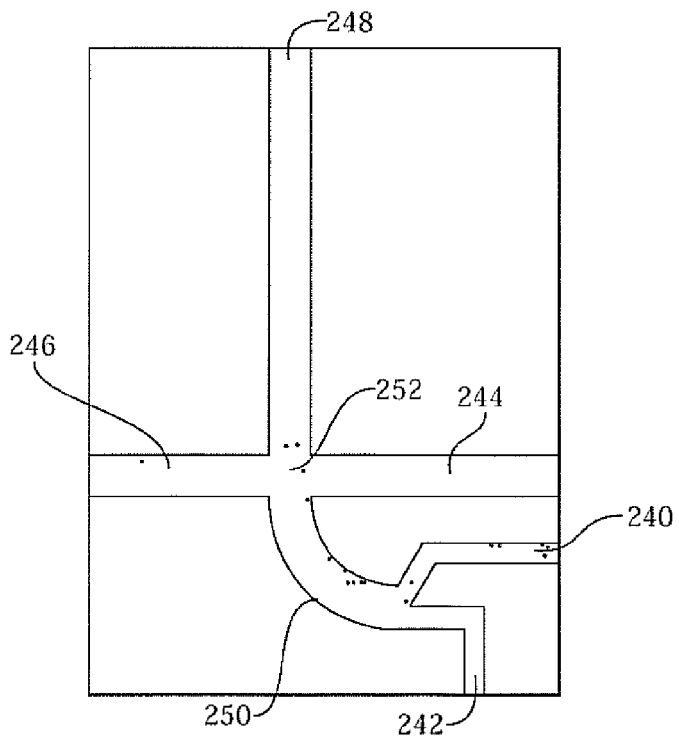

The flow patterns in both fluorescent image (FIG. 6A) and bright field image (FIG. 6B) show the "drifting" behavior of the particles in the curved channel which match the flow pattern obtained using the fluorescent dye previously described, suggesting a successfully 3D particle focusing. The image of FIG. 6A was taken over a long exposure time (200 milliseconds), showing sample flow 220. Figure GB shows sample flow input 240, sheathing flow inputs 242, 244, 246, and output flow channel 248.

Figure 7A:
FIGS. 7A-7B show side-view imaging of the 3D hydrodynamic focusing of microparticles.
Figure 7B:

FIGS. 7A and 7B show a side-view imaging test of the 3D particle hydrodynamic focusing, conducted using the same setup as previously described above in relation to FIGS. 2-3. FIG. 7A shows that a particle can be effectively focused in the center of the channel, shown at 260. When the flow injection is stopped, the particles are not longer vertically focused and particles travel through the channel at different height, shown as the lighter region 262. Most particles travel in the region closer to channel bottom due to gravity, as compared to the previously described small fluorescein molecules which were uniformly distributed in the entire channel in FIG. 3D.

Hence, a novel "microfluidic drifting" technique can be effectively used in focusing not only small molecules, but also larger microparticles such as biological cells. A microfluidic drifting approach is readily applicable for 3D hydrodynamic focusing of biological molecules for single molecule detection as well as biological cells for microfluidics based flow cytometry devices.

Example Device Fabrication

Polydimethylsiloxane (PDMS) microchannels were fabricated using a standard soft lithography technique. The master mold for the soft lithography was made on a silicon wafer (TechGophers, Chino Hills, Calif.) by Deep Reactive Ion Etching (DRIE, Adixen, Hingham, Mass.). The positive photoresist Shipley 1827 (MicroChem, Newton, Mass.) was lithographically patterned on the silicon wafer to act as a mask for DRIE, and the etch depth was set at 75 µm. The final mold depth was measured using a profilometer (KLA-Tencor, San Jose, Calif.) to ensure that the desired depth had been achieved.

The silicon mold was subsequently coated with 1H,1H,2H, 2H-perfluorooctyl-trichlorosilane (Sigma Aldrich, St. Louis, Mo.) after DRIE, in order to reduce surface energy and hence the damage to the PDMS channel during the demolding process. A smooth surface of the PDMS channel sidewall reduces scattering losses and improves the quality of side-view epifluorescence microscopy. Sylgard™ 184 Silicone Elastomer Base and Sylgard™ 184 Silicone Elastomer Curing Agent (Dow Corning, Midland, Mich.) were mixed at a 10:1 weight ratio, cast onto the silicon mold, and cured at 70° C. for 2 hours. After the PDMS channel was hardened, it was peeled from the mold. Inlets and outlets were drilled with a silicon carbide drill bit and the channel was subsequently sealed onto a glass slide. Polyethylene tubes (Becton Dickson, Franklin Lakes, N.J.) were inserted into the inlets to connect the device to a syringe pump (KDS 210, KD Scientific, Holliston, Mass.).

A 2 mm×2 mm 90-degree prism (Edmund Optics, Barrington, N.J.) was placed adjacent to the optical window to reflect the excitation light (wavelength=488 nm) from the microscope lens into the microfluidic channel and the emission light (wavelength=525 nm) from the 3D focused flow downward into the microscope lens. Still images and a real-time video of the 3D focusing process were recorded using an inverted microscope (TE 2000U, Nikon, Melville, N.Y.) and a CCD camera (CoolSNAP HQ2, Photometrics, Tucson, Ariz.).

Applications

Hydrodynamic focusing is extremely useful for various microfluidics applications, such as chemical/biological analyses, including on-chip flow cytometry, single molecule detection, and laminar mixers for the study of rapid chemical and enzymatic kinetics. Improved microfabrication procedures described herein allow for three-dimensional (3D) hydrodynamic focusing devices with the ability to focus the sample flow in the vertical direction, and allow 3D on-chip manipulation of the sample flow.

The planar nature of a microfluidic network fabricated via standard soft lithography only facilitates two-dimensional (2D) hydrodynamic focusing horizontally (in-plane) compression of the inner sample flow into a thin "sheet" between two sheath flows injected from both sides of the sample flow. There is no ability to focus the sample flow in the vertical (out-of-plane) direction. 3D focusing may be achieved by delivering sheath flows from both vertical and horizontal directions using a multi-layer microfluidic device. Such methods require either tedious assembly of individual components or multiple alignments and exposures during mold fabrication. These limitations significantly increase the cost and complexity of the device and ultimately severely hinder their applicability.

For many applications, 2D hydrodynamic focusing alone is intrinsically problematic due to the lack of vertical focusing. For example, the non-uniform velocity distribution of vertically spread cells or molecules is known to cause problems in flow cytometry.

A microfluidic device according to the present invention may be an analytical instrument, such as a spectrometer, for example a fluorescence spectrometer or a laser spectrometer. A microfluidic device may further be a flow cytometer, laminar mixer, a reaction vessel, or a chemical processing device.

Three-dimensional hydrodynamic focusing is useful for microfluidics-based flow cytometry system. In conventional flow cytometry, 3D hydrodynamic focusing is achieved using a co-axial structure. However, such structures are difficult to implement using the standard soft-lithography technique, which only facilitates the 2D planar fluidic structures. However, the novel hydrodynamic focusing technique using microfluidic drifting enables 3D hydrodynamic focusing in a single-layer two-dimensional (2D) planar microfluidic structure, something never before achieved in conventional microfluidic devices. 3D hydrodynamic focusing can be achieved for molecular solutions, as shown using a fluorescent dye solution, and the same approach can be used for the 3D focusing of discrete microparticles, such as lymphocytes which are routinely screened in HIV diagnosis using flow cytometry.

Novel 3D focusing techniques described herein are particularly useful for on-chip single molecule detection, which requires passage of the sample through an optical detection region that is much smaller than the channel size. In conventional microfluidic devices, the vertical spread of sample results in a large number of undetected molecules. However, the vertical focusing provided by examples of the present invention avoids such problems, and allows accurate single molecule detection.

Other Aspects

Examples of the invention include novel apparatus and methods to implement three dimensional (3D) hydrodynamic focusing a single-layer planar microfluidic device, which can be fabricated using a standard soft-lithography technique.

An improved microfluidic device comprises a curved channel section operable to focus a sample flow in an out-of-plane direction, compressing the flow in a direction generally normal to a plane including the curved channel (such as a plane parallel to the substrate). An improved microfluidic device operable to provide three-dimensional hydrodynamic focusing of a sample flow uses a vertical focusing sheath flow and at least one horizontal focusing sheath flow, flows being generally coplanar and being conveyed within channels of a planar device. Unlike conventional devices, no out-of-plane sheath flow or multilayer structures are required.

Embodiments of the present invention include improved flow cytometers and other cell characterization devices, improved single molecule detection devices, other analyte characterization devices, analyte sorting devices, genetic analysis devices, and the like. An analyte may be a molecule (such as a small molecule, polymer, biomolecule), biological structure (such as a cell, for example a blood cell), particle (of any type), and the like. A radiation beam, such as a laser, may be directed through the narrow portions of a focused flow. Scattering, fluorescence, or other property may be monitored.

In a laminar mixer, flow velocity variations of the focused enzymes or chemical species in the vertical direction may result in a different reaction time across the depth of the channel, which would make it extremely difficult to extract meaningful information of reaction kinetics. Hence, an improved laminar mixer according to an embodiment of the present invention includes a curved channel for inducing hydrodynamic focusing.

An example microfluidic device, operable to provide three-dimensional hydrodynamic focusing of a sample flow, includes a first channel having a curved channel section operable to provide hydrodynamic focusing of the sample flow in a direction out of a plane including the curved channel. The device may be a planar microfluidic device. The device may further include a second channel crossing the first channel, the second channel operable to convey a sheath flow inducing in-plane hydrodynamic focusing of the sample flow.

Example apparatus according to the present invention include a flow cytometer, a fluorescence spectrometer, a laser spectrometer, a laminar mixer, a reaction vessel, or a chemical processing device. Other examples will be apparent to those skilled in the art.

A curved channel within an improved apparatus may, for example, have a generally rectangular or square cross-section. The channel width and/or height may be in the range 100 nm-1 mm, for example in the range 1 micron-500 microns. The mean radius of the curved channel may be in the range 1 micron-1 mm, for example in the range 10 microns-500 microns. The curved channel may have a lower wall parallel to and proximate the substrate, a curved inner side wall, a curved outer side wall (the outer side wall having a radius of curvature greater than the inner side wall), and an upper wall opposite the lower wall and generally parallel to the substrate. The terms upper and lower are used for illustrative simplicity and are not intended to be limiting. The sample flow and first sheath flow may be introduced so that the sample flow is initially closer to the inner wall. The fluid interface between the sample flow and the first sheath flow may initially be vertical (as used in this example, the term vertical refers to a direction normal to the substrate). However, as the sample flow and the first sheath flow pass through the curved channel, the fluid interface tends to curve outwards, towards the outer wall, for example as discussed in relation to FIG. 1. At the end of the curved channel, it is possible to obtain a sample flow centered between the upper and lower walls, with the first sheath flow split into a layer further from the substrate and a layer nearer the substrate than the sample flow. The sample flow is compressed so as to be a layer extended generally parallel to the substrate, and may be centered in the channel along a vertical direction. Hence, the sample flow becomes compressed (narrowed) as measured along a direction normal to the substrate, which may be termed vertical hydrodynamic focusing, though the term "vertical" here represents a direction normal to the substrate and is not otherwise intended to be limiting.

An example microfluidic device includes a first channel having a curved channel section, the curved channel section being operable to provide hydrodynamic focusing in a focus plane, the focus plane being non-parallel to a plane including the curved channel section. The device may include a substrate, the focus plane being generally normal to the substrate. The device may have an inlet for a sample flow, and an inlet for a vertical focusing sheath flow. The device may further including a second channel crossing the first channel, the second channel having at least one inlet for a horizontal focusing sheath flow.

A method of three-dimensional hydrofluidic focusing of a sample flow comprises passing the sample flow and a first sheath flow through a curved channel section; and passing the sample flow through a second sheath flow, the second sheath crossing the sample flow, the curved channel section and second sheath flow cooperatively providing three-dimensional hydrofluidic focusing of the sample flow.

A method of hydrofluidic focusing a sample flow in a planar microfluidic device having a planar substrate comprises passing the sample flow and a sheath flow through a curved channel section disposed on the planar substrate, the curved channel section providing hydrofluidic focusing of the sample flow in a direction generally normal to the planar substrate, The method may further comprise hydrofluidic focusing in an in-plane direction, for example using a pair of sheath flows within a linear flow channel.

A further example of the present invention is an apparatus comprising a plurality of 3D hydrodynamic focusing components, and in some example two or more focused sample flows may intersect or otherwise interact.

Examples of the present invention include apparatus and methods for flow cytometry, and apparatus for counting, analysis, and sorting of particles in the sample flow (e.g. microscopic particles such as cells, molecules, biomolecules, and the like) suspended in the sample flow. Particles may be labeled, for example with a fluorescent marker, or otherwise functionalized. For example, biological macromolecules may be fluorescently tagged and detected in the sample flow.

Example apparatus may include a radiation source (such as a laser), and a radiation beam may be directed into the main channel at or proximate the point of hydrodynamic focus. One or more detectors may be configured to receive detected radiation, which may comprise transmitted, scattered and/or fluorescent radiation. An electronic circuit, such as a computer, may be used to analyze detector signals, so as to determine properties of the particles. For example, cell dimensions and other properties may be determined, and particles may be imaged, reacted, or otherwise processed.

Examples of the present invention include high-throughput cell cytometers, single-molecule fluorescent spectrometers, genetic analyzers, fluorescence-activated cell sorters, and other applications. In some examples, particles having detected properties may be counted, extracted, sorted, or otherwise processed. In some examples, a plurality of radiation sources, such as lasers, and associated detectors may be used.

An example microfluidic device is operable to provide three-dimensional hydrodynamic focusing of a sample flow using a first (vertical) focusing sheath flow and one or more horizontal focusing sheath flows, the sample flow, vertical focusing sheath flow and the horizontal focusing sheath flow (s) being generally coplanar. This enables the device to be more simply fabricated than previous approaches, for example as a single layer device in which all flow channels may be generally coplanar.

Flow Cytometry Apparatus

An integrated, single-layer, miniature flow cytometry device capable of multi-parametric particle analysis was fabricated. The device integrates both particle focusing and detection components on-chip, which includes a microfluidic drifting based three-dimensional (3D) hydrodynamic focusing stage and a series of optical fibers integrated in the microfluidic architecture to facilitate on-chip detection. Multiple optical signals (i.e., forward scatter, side scatter, and fluorescence) from individual particles can be simultaneously detected.

Experimental results indicated that the performance of the flow cytometry chip was comparable to an expensive desktop counterpart. The integration of on-chip particle focusing with on-chip multi-parametric optical detection in a single-layer, mass-producible microfluidic device allows low-cost flow cytometry chips for point-of-care clinical diagnostics.

Flow cytometry is a powerful, high-throughput tool that can perform both quantitative and qualitative multi-parametric analyses of individual cells (or other particles). In an example apparatus, the focused cells pass through a laser beam, generating three types of output optical signals: forward scatter (FSC), side scatter (SSC), and fluorescence (FL). FSC is the light deflected by a cell at a small angle (2-20°) relative to the input laser beam. The intensity of the FSC signal is indicative of the size and refractive index of the cells. SSC is the light diffused in all directions due to cellular granularity. FL can be collected using the same optics as SSC and is later split to different detectors based on the light frequency. Each of these detection signals (FSC, SSC, and FL) is eventually processed to identify individual cells in a mixed cell population based on cell size, granularity, and various fluorescence markers.

Flow cytometry can be used for various biological studies and clinical applications, including aiding in the diagnosis of potentially fatal diseases like leukemia, HIV, and assessing cellular phenotypes prior to and during the course of therapeutic interventions. However, conventional apparatus are high cost and bulky, with mechanical complexity and need for highly trained personnel. Limitations of conventional apparatus limited the use of this technique to well-equipped, centralized laboratories.

Three-dimensional (3D) hydrodynamic focusing, or microfluidic drifting, is well suited for use in improved flow cytometers. Using the Dean flow in a curved microfluidic channel, microfluidic drifting enables 3D hydrodynamic focusing in a single-layer planar microfluidic device that can be readily fabricated via standard soft-lithography. A microfluidic drifting based 3D hydrodynamic focusing device may be combined with an off-chip laser-induced fluorescence detection system to give a miniature flow cytometer. However, examples of the present invention further include a single-layer flow cytometry chip that includes both particle focusing and multi-parametric detection components integrated on-chip.

An example on-chip flow cytometer employs a fiber optic-based, on-chip detection system that can be seamlessly integrated with the microfluidic drifting stage in a single-layer planar microfluidic device. In addition, the integrated flow cytometer can achieve multi-parametric detection of three output optical signals (FSC, SSC, and FL) from individual particles simultaneously. The device offers a significant size reduction and simple fabrication procedure, and large reductions in required cell sample and reagent volumes, all of which contribute to the remarkably reduced cost of devices according to examples of the invention.

FIG. 8 shows the configuration of an example flow cytometry chip. The device is an integrated microfluidic device including particle focusing and particle characterization stages, and may in some examples be followed by an integrated particle sorting stage. The device includes two stages: the fluidic focusing stage shown generally at 300 and the optical fiber-based on-chip detection module shown generally at 302. The microfluidic drifting based 3D hydrodynamic focusing stage 300 uses microfluidic drifting for 3D particle focusing within a single-layer microfluidic device. The particle flow and vertical-focusing sheath flows are injected side-by-side from inlets A and B, respectively. The two flows converge and enter the curved channel 303, in this example a 90-degree curve. As described further elsewhere, other curve angles may be used.

In the curved channel 303, the induced Dean flow, characterized by double-ring vortices in the cross-sectional plane, sweeps the particles from the top and bottom of the channel toward the center plane of the channel. This step is termed microfluidic drifting and effectively focuses the flowing particles in the vertical direction. The particles are pushed into a single line of particles by the horizontal sheath flows C and D. Thus this two-step procedure results in 3D focusing of the particles within a single-planar microfluidic channel. The insets 312, 314, 316, and 318 are schematics of typical particle distributions at the planes labeled 1, 2, 3, and 4, respectively. Inset 314 shows the counter-rotating vortex flows. The detection point 310, in output channel 308, is where the particle flow is illuminated, and from where optical signals are detected.

FIG. 8 also shows the fiber-based on-chip detection module 302, including four optical fibers: the input fiber 304 and three detection fibers 305, 306, and 307. The input fiber has a small numerical aperture (NA) and is inserted perpendicular to the channel to deliver the excitation light to the focused cell stream. The excitation light is generated from an argon laser (488 nm) and coupled into the input fiber via a fiber coupler. Other lasers may be used, such as a diode laser. The three detection fibers are arranged around the main channel at different angles so that the FSC (fiber 307), SSC (fiber 306), and FL (fiber 305) signals can be simultaneously detected. The FSC fiber 307 is fixed at 20° from the direction of propagation of the excitation laser beam to collect forward-scattering light from the excited particles without collecting the directly transmitted light. The SSC and FL fibers (306 and 305, respectively) are arranged 60° and 120° from the direction of propagation to collect the side-scattering light and fluorescent emission, respectively. The collected FSC, SSC, and FL signals are transmitted through their designated fibers and a band-pass filter (488 nm filter for FSC and SSC, and 532 nm filter for FL) before they are detected by photomultiplier tubes (PMTs).

Examples of the present invention may use other excitation sources, such as other lasers (e.g. diode lasers), light emitting diodes, and the like. Other detectors may be used, such as semiconductor optical sensors such as photodiodes. Video and/or imaging sensors may also be included for some applications if desired.

FIG. 9A is an optical image taken of the integrated and assembled flow cytometry chip, whose size is comparable to a U.S. quarter.

FIG. 9B shows a microscopic image illustrating hydrodynamic focusing due to the horizontal- and vertical-focusing sheath flows. FIG. 9B also shows the arrangement of the input fiber (304) and the three detection fibers (e.g. 307) around the fluidic channel.

Figure 10A:
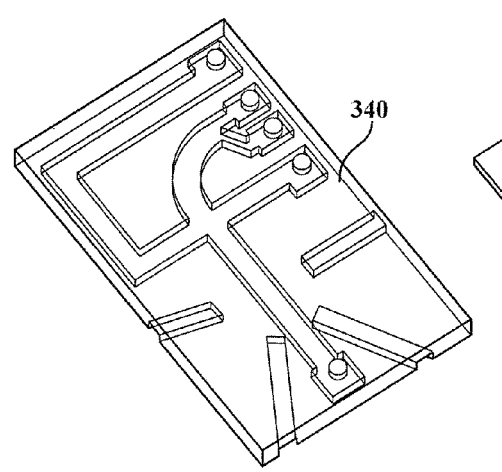
FIGS. 10A-10D illustrate a fabrication procedure for the flow cytometry chip, FIG. 10A showing a PDMS layer for fluidic channel/fiber-insertion channel, FIG. 10B showing the PDMS layer sealed with a glass substrate, FIG. 10C showing insertion of fluidic tubings, and FIG. 10C showing insertion of optical fibers.
Figure 10B:
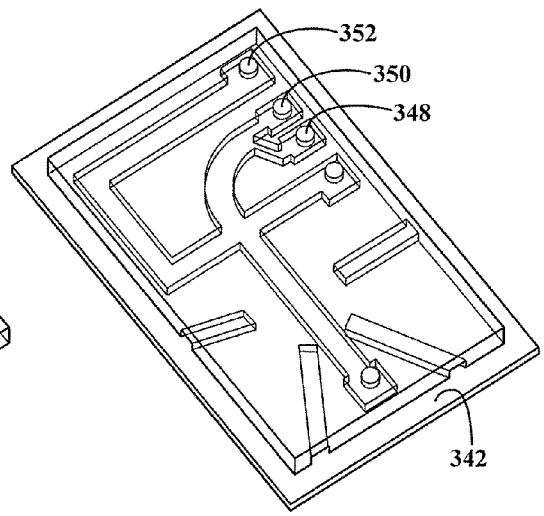
Figure 10C:
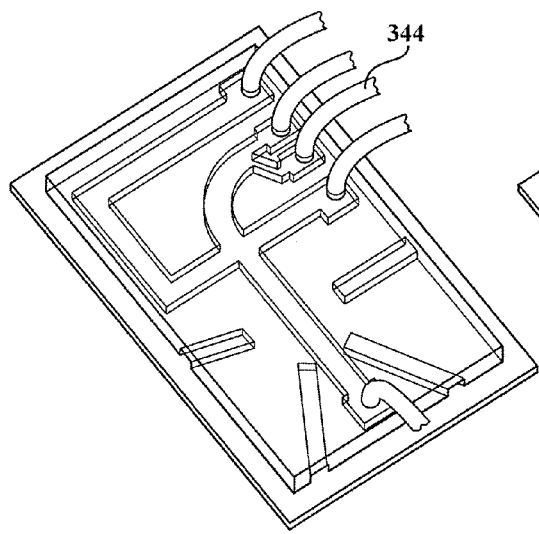
Figure 10D:
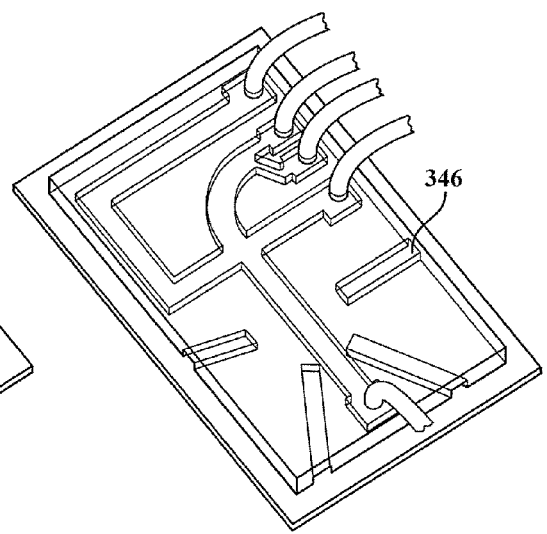

FIGS. 10A-10D show a schematic of the fabrication procedure for the flow cytometry chip. The procedure includes four steps. FIG. 10A shows fabricating PDMS layer 340 for fluidic channels and fiber-insertion channels. FIG. 10B shows sealing the PDMS layer with a glass substrate 342. FIG. 10C shows inserting fluidic tubings 344 into the microfluidic chip, and FIG. 10D shows inserting optical fibers (e.g. 346) into the microfluidic chip.

In the illustrated example, each inlet (vertical sheath flow 350 and sample flow inlet 348) is 80 μm in width and merge together forming a main channel of 167 μm, while the side sheath flow inlets (such as 352) also measure 167 μm in width. The single-layered microfluidic chip was fabricated from PDMS using a standard soft lithography technique. The master mold was made via deep reactive ion etching (DRIE) of a silicon wafer to a depth of 129 μm, thus maintaining a width to height ratio of roughly 4:3. To facilitate the removal of the cured PDMS from the mold, the surface of the mold was silanized by 1H,1H,2H,2H-perfluorooctyl-trichlorosolane vapor. A Harris unicore punch (0.75 mm) was used to make holes for the fluid inlets and the outlets in the PDMS channel, and used polyethylene tubings for the inlet and outlet flows.

The following optical fibers were used: (1) single-mode input fiber, Thorlabs S405, core diameter=2.9 μm, cladding diameter=125 μm, and NA=0.14; and (2) three multi-mode detection fibers, Thorlabs AFS105.125Y, core diameter=105 μm, cladding diameter=125 μm, and NA=0.22.

The input fiber has a relatively small NA (0.14) so that the excitation laser does not expand significantly (angle of light cone ~16° with width of ~25 μm at the detection point) by the time it reaches the detection point; this eliminates the need for on-chip lenses for light focusing. The NA of the three detection fibers is relatively large (NA=0.22) so that a higher light-collection efficiency is achieved. Three PMTs (Hamamatsu 6780-20) were driven by a homemade control circuit where their gains could be individually controlled. The PMT signals were first amplified with a high-frequency amplifier (Hamamatsu C6438-01) and recorded using a digital oscilloscope (Tektronix DPO400). The height of the channel was set at 129 μm so that fibers with a diameter of 125 μm could be inserted in the fiber-insertion channels.

Fluorescent (dragon green, excitation=480 nm, emission=520 nm) polystyrene microparticles with two different nominal diameters of 7.32 µm (particle #1) and 15.5 µm (particle #2) were purchased from Bangs Laboratories. These two sizes were carefully selected to cover the entire size range of human blood cells (e.g., lymphocyte ~7-8 µm, monocyte ~14-17 µm). The experiments were performed with a 1:1 mixture of particle #1 and particle #2. The mixed particles were diluted in a 0.01% SDS solution to a final concentration of ~3×106 particles ml$^{-1}$ and sonicated for 10 min prior to experiments to prevent particle aggregation.

The performance of the flow cytometry chip was characterized using commercial fluorescent microparticles. The particle solution was injected through the particle inlet A at a flow rate of 30.0 µl min$^{-1}$, whereas the vertical-focusing sheath flow rate was 370 µl min$^{-1}$ (Inlet B) and the horizontal-focusing sheath flow was 255 µl min$^{-1}$ (Inlets C and D). For each test, data was recorded for 4 s at a sampling rate of 2.5 MHz and analyzed with a program written in MATLAB. All three light signals were simultaneously detected and recorded. Two distinctive groups of peaks, each with their own characteristic height, were identified in all three channels (FSC, FL, and SSC). Each group represents different sized fluorescent particles. Each group of peaks showed similar profiles, a pulse width of ~43 µs for the large particles and ~30 µs for the smaller particles. A four-second data set recorded a total number of 2738 particles (685 particles s$^{-1}$). Under the studied experimental conditions, detection events were well separated, indicating a great potential to further improve the throughput of the system simply by increasing the concentration of the particles/cells. Assuming a minimum peak-to-peak interval to be three times the peak width in order to resolve two neighboring peaks, the maximum detection throughput of the system may be estimated as 1 s/(3×43 µs), or ~8,000 events s$^{-1}$ under the flow conditions used.

Experimental results of our device were compared with a commercial flow cytometry device (Beckman-Coulter FC500, unit price ~$100,000). Three-dimensional scatter plots of all detected events (FSC+FL+SSC) revealed the performance of the flow cytometry device as comparable to a commercial flow cytometer. Detection events could be grouped into two distinct regions of the scatter plots for FSC versus FL versus SSC, corresponding to two particle species. For the fabricated flow cytometry device, the peak count ratio is 43.5% for particle #1, 53.9% for the particle #2, and 2.52% for the "doublets" (aggregation of two or more small particles, represented by green dots). For the commercial flow cytometry device the peak count ratio is 44.7% for particle #1, 52.4% for particle #2, and 2.85% for the doublets.

Hence, the results of the fabricated device matched the experimental condition (1:1 mixing ratio), and the data from the commercial flow cytometer (FC500, Beckman Coulter, Brea, Calif.).

TABLE 1

| CV | Flow Cytometry Chip | Beckman Coulter FC500 |
| --- | --- | --- |
| FSC, Particle #1 | 9.1% | 4.2% |
| FSC, Particle #2 | 6.8% | 4.5% |
| SSC, Particle #1 | 17.1% | 13.2% |
| SSC, Particle #2 | 16.4% | 13.3% |
| FL, Particle #1 | 8.1% | 5.6% |
| FL, Particle #2 | 6.3% | 5.9% |

Table 1 (above) shows a comparison of coefficients of variation (CV), an indirect measure of the repeatability and precision of the flow cytometry system, for all parameters obtained from both the commercial flow cytometer and the flow cytometry chip. The data show that the commercial flow cytometer is still slightly better than the flow cytometry chip in terms of CV. This observation is likely due to the fluctuation of particles in the focused stream in our flow cytometry chip; the width of the focused stream is around 20 µm under current flow conditions and larger than the diameters of both small and large particles. This hypothesis is supported by the fact that for both our flow cytometry chip and the commercial one, the larger particles (Particle #2, diameter=15.5 µm) have smaller CV than the smaller particles (Particle #1, diameter=7.32 µm). Nevertheless, lower CV can be achieved by optimizing the flow conditions in our flow cytometry chip to obtain a smaller focused stream, depending on the application of future usage.

In conclusion, an integrated, multi-parametric flow cytometry chip was designed and fabricated. The device integrated microfluidic drifting based on-chip 3D hydrodynamic focusing with fiber-based on-chip optical detection. The flow cytometry chip can simultaneously detect FSC, SSC, and FL signals from individual particles and was able to distinguish between the two groups of particles. An example device achieved a detection throughput of 685 particles/s, with a potential detection throughput of 8,000 particles s$^{-1}$ under flow conditions used.

Compared to conventional flow cytometers, an integrated device has significant advantages in both size and cost. Examples include chip-sized, low-cost flow cytometry for point-of-care clinical use. A flow cytometry chip enables decentralized flow cytometry applications, and allows transformative impact on both fundamental biological research and clinical diagnostics.

Curvature of Microfluidic Focusing Devices

Examples of the present invention include microfluidic devices with optimized curved channels, and include a 180°, n-turn, microfluidic-based flow cytometry device capable of focusing microorganisms as small as bacteria (1 micron), where n is any real number A flow cytometer can detect single cells at very high speed. An example improved flow cytometry device is a microfluidic, single-layered, on-chip device that is capable of cell/particle focusing hydrodynamic focusing.

The full effectiveness of a flow cytometer can only be realized if the cells or particles pass, one-by-one, through a particular point called the interrogation point. Commercial flow cytometry devices achieve this by passing fluid containing the cells/particles through a small tube that has large concentric outer tubing through which the sheath fluid flows. Increasing the sheath flow rate increases the tightening of the core flow. Sheath fluids are extremely expensive and mainly contribute to the increasingly high running cost inherent with present flow cytometers. This increase in cost greatly affects the accessibility of this device as a routine test, and thus a higher rate of death occurs due to lack of sufficiently expedient diagnoses of victims. Therefore, it is imperative that this problem be overcome in order to substantially increase efficiency and quality of medical care, and in doing so, increase overall quality of human life.

Examples of the present invention include a microfluidic-based device with high throughput and much lower running cost compared to conventional devices, without compromising the results, the quality of which depends on the focusing width of the flow cytometry device.

In consideration of life threatening diseases, examples of the present invention may be used to identify of cells characteristic of diseases, such as cells affected by HIV, cancerous tumor cells, and the like. Examples of the improved design allow improved particle focusing (with smaller focus width of ~1 μm), and detection achievability for extremely small microorganisms comparable to the typical size of bacteria, around 1 micron.

Moreover, optimization through simulations allows effective practical testing of the device, validating the described improvements.

The total flow rate may be reduced by 50%, and vertical sheath flow by more than 76%, by optimization of the curved channel properties relative to a 90° curved channel. Guidelines were developed for designing single-layered, on-chip, hydrodynamic-based flow cytometry chips. By following these guidelines, and by extrapolating from the graphs presented in this document, flow cytometry devices can be build that far surpass the performance of the commercial flow cytometer.

Initial flow cytometry studies showed a focusing width, measured via confocal microscopy, of 25 microns. A smaller focusing width is preferred for focusing particles and cells smaller than 15 microns. A solution to the size limitation factor was developed, allowing guidelines for developing improved flow cytometry devices using microfluidic-based, single-layered, on-chip devices providing the same utility as commercial flow cytometry, with the added benefit of more economical use of the sheath fluids.

In the case of curved microfluidic channels, above a certain fluid flow velocity, secondary fluid behaviors in terms of counter-rotating vortices are observed. The term that describes this phenomenon is often related with the expression called the "Dean number" (De), which is given as:

$$De = \frac{\rho VD}{\mu}\left(\frac{D}{2R}\right)^{1/2}$$

where ρ is the density of the fluid, μ is the dynamic viscosity, V is the axial velocity scale, D is the diameter (other shapes are represented by an equivalent diameter), and R is the radius of curvature of the path of the channel.

The Dean number is an integration of the expression of the Reynolds number with the radius of curvature. For a straight channel, where the radius of curvature is zero, the resulting Dean number is undefined, signifying the absence of counter-rotating vortices and lack of secondary flow within the channel. Secondary flow only becomes significantly observable above a certain value of flow velocity.

In the case of microfluidics, since we are mostly dealing with channels that have a rectangular cross-section, D is the hydraulic diameter, given by the expression D=(2wh)/(w+h), where w and h are the channel width and height, respectively. A cross-sectional view of a typical curved channel demonstrates counter-rotating vortices that form the secondary fluid motion.

The Dean number is a measure of secondary convective flow. A higher Dean number indicates higher velocity of the counter-rotating velocity. This number may be controlled by manipulation of the curvature length (curved channel bend angle) to achieve the desired objectives. The expression for the Dean number includes the radius of curvature, which is enclosed inside the square root in the denominator. Thus, by changing the radius of curvature, one can alter the sheath flow. By increasing the radius of curvature, the vertical sheath flow is decreased. Increasing the radius of curvature would increase the overall size of the device. Therefore, a different route to achieve the same effect was realized, by increasing the curvature length of the channel. Increasing the curvature length, in essence, gives more time for the centrifugal force to act over the same fluid. The fluid near the inner wall undergoes greater force than that which is near the outer channel wall. The constraints of the channel dimension therefore cause counter-rotating vortices to appear. Thus, by increasing the curvature length, a much greater degree of focusing in the vertical direction can be achieved, since the centripetal force acts for a longer time than in the case of shorter curvature length. This however, still occurs at lower vertical sheath flow. Upon effective vertical focusing, the side horizontal sheath fluids then compress the vertically focused fluid into a centralized thin stream of fluid focused in the center of the channel.

Using this strategy, it was shown that much improved channel focusing can be achieved with 135°, 180°, 235° . . . 180° n channel curvature lengths, where n is any real number. Up to the 235° channel curvature length, a channel aspect ratio of 4:3 (width: height) was used. However, beyond this curvature length, a higher aspect ratio is preferred.

Figure 11B:
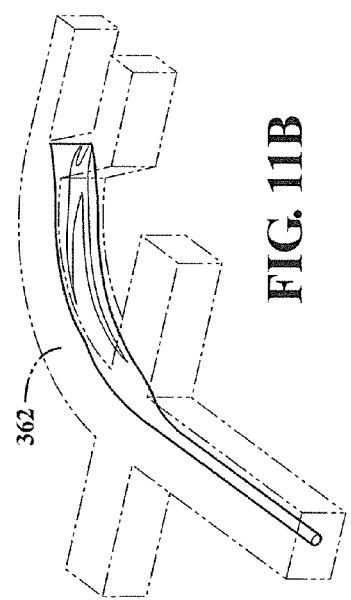
FIGS. 11A-B show simulation results that have been optimized for sheath flow.
Figure 11D:
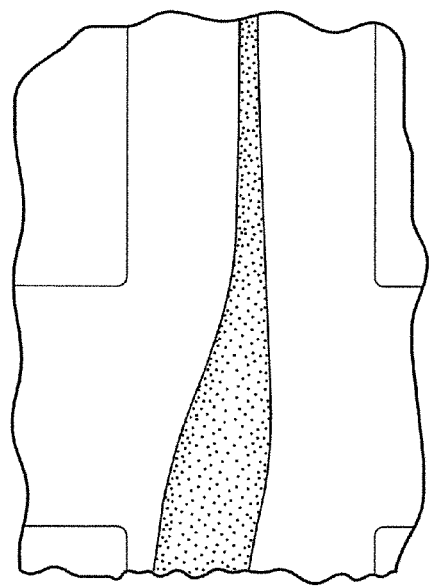
FIG. 11D shows the z-stack of images taken at 100000 fps, showing that 7-micron polystyrene beads focus in the center of the channel, confirming the results from the simulations.
Figure 11A:
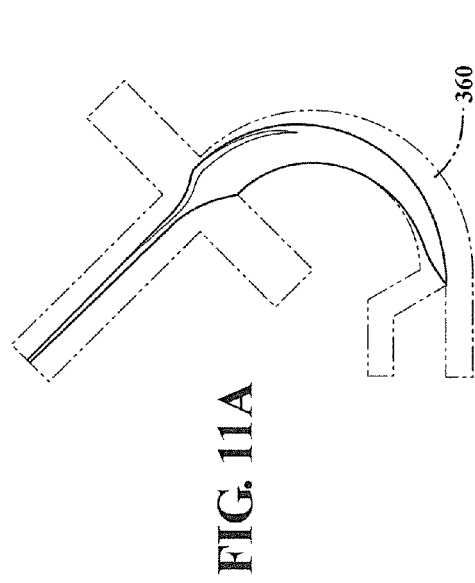

FIGS. 11A-D are detailed overview of the optimized results achieved by simulations and verified through experimentation for a device with a curvature length of 135°. FIGS. 11A-B show hydrodynamic focusing simulations. The increased curvature design (135°) of FIG. 11A, having a curved channel of bend angle 135°, denoted 360) results in centrifugal force acting over a time period greater than that seen with the 90° curvature (curved channel 362, FIG. 11B), thus allowing for a reduction in the vertical sheath flow by 45%, while also giving a reduced focusing width of 6.5 microns. The smaller focusing width is due to a tighter vertical focusing step, followed by horizontal fluids compressing that thin layer of fluid into a centralized focusing width of 6.5 microns. Thus, by increasing the curvature length from 90° to 135°, focusing width reduces from 25 microns to 6.5 microns.

Figure 11C:
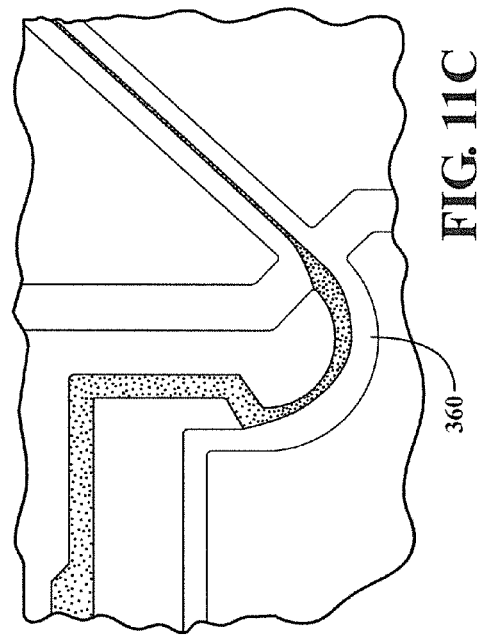
FIG. 11C shows an optical microscope image of a 135° curvature device showing the congruency with the simulation results having a focusing width of 6 microns.

FIG. 11C is an optical microscope image, with ink being used as the sample fluid to validate the simulations. FIG. 11D is the z-stack of images of video taken at 100,000 fps showing the focusing of polystyrene beads into a stream of approximately 7 microns.

Figure 12A:
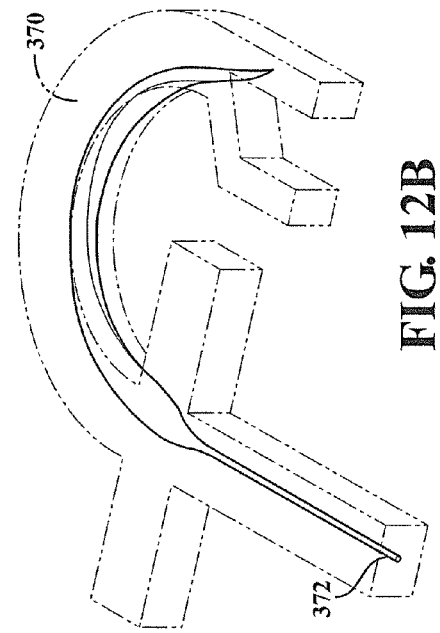
FIGS. 12A-B show the simulation results optimized for a vertical sheath flow reduction of 70% to achieve a focusing width of 1.5 microns.
Figure 12B:
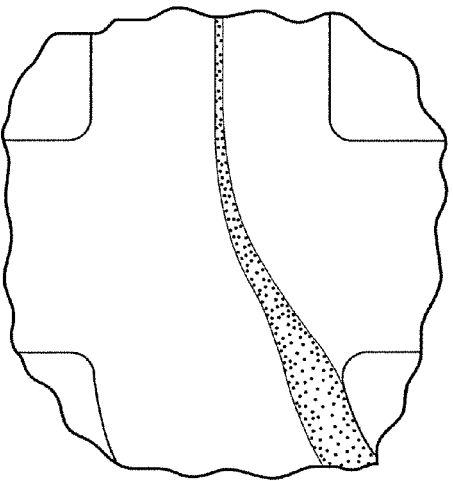
Figure 12C:
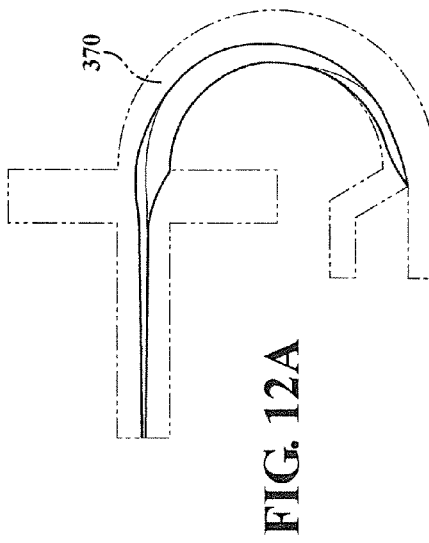
FIG. 12C shows an optical microscopic image of a 180° curvature device confirming the results shown by simulations. The dark fluid is the ink used to show the path of the focused sample fluid.
Figure 12D:
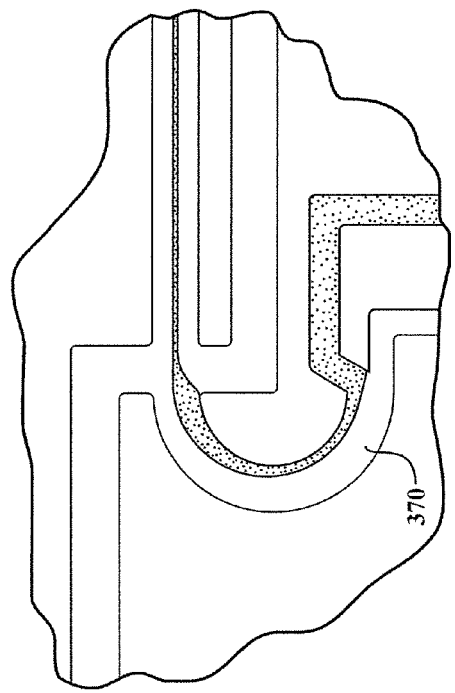
FIG. 12D shows the z-stack of 1.9-micron polystyrene beads being focused in the center of the channel.

FIGS. 12A-D show detailed imagery of simulation results using a curvature length of 180° (curved channel 370 in FIG. 12A), showing that a focusing width of 1.5 microns is achieved with an optimized vertical sheath flow reduction of 70 percent. FIG. 12C is an optical microscope image with ink being used as the sample fluid to validate the simulations. FIG. 12D is the z stack of images of video taken at 100,000 fps showing the focusing of polystyrene beads of 1.9 micron being focused into a stream of approximately 2 microns.

Figure 13A:
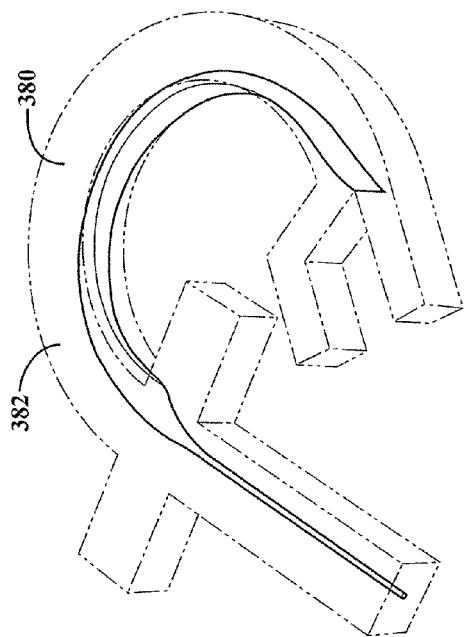
FIG. 13 shows simulation results using a curvature length (curved channel bend angle) of 235°, achieving a focusing width of 1.5 microns with vertical sheath flow reduction of as low as 76% as compared to that of a 90° curvature device.
Figure 13B:
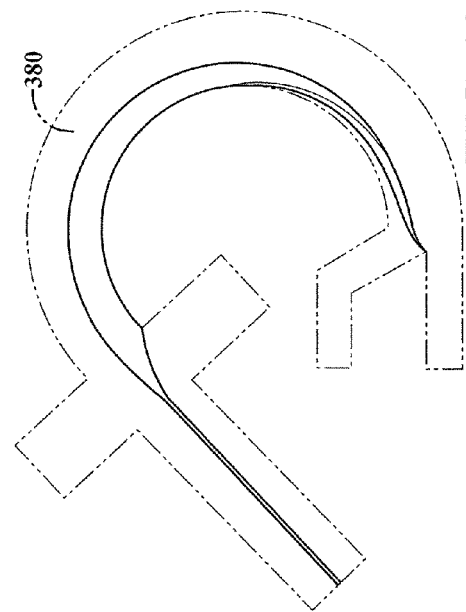

FIGS. 13A-B show the simulation results of a channel with curvature length of 235° (curved channel 380), indicating a focus width of 1.5 microns with a vertical sheath flow reduction of 76%. FIG. 13B shows a slice 382, where cross-sectional flow profiles were examined.

All of the above results were obtained using main channel dimensions of 100 microns (width) by 75 microns (height). From the expression for the Dean number, the radius of curvature affects the counter-rotating vortices. Thus, for a particular curvature length (say 90°), in order to achieve focusing in the channel center, a general guideline is to maintain the Dean number and perform back calculations for the vertical sheath flow. It is therefore apparent from the Dean number expression, that decreasing the radius of curvature calls for an increase in the vertical sheath flow in order to initially achieve effective vertical focusing, and vice versa.

Having proven the cases for 90°, 135° and 180° experimentally, and due to the fact that experimental results were in congruence with the simulated results, it is reasonable to perform simulation for all other cases to provide complete guidelines showing the effect of varying radii of curvature and/or curvature length.

Figure 14A:
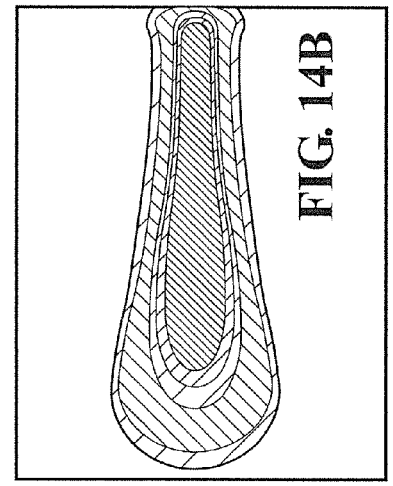
FIG. 14A shows simulation results showing the effect of a low Dean number where no remixing is occurring.
Figure 14B:
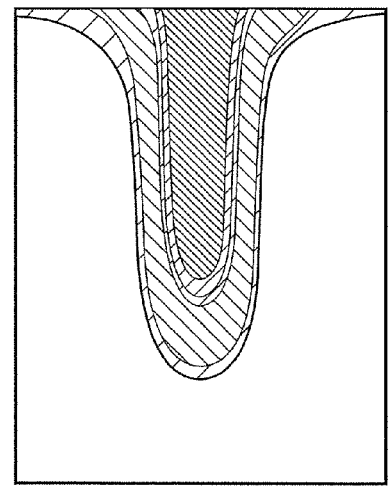
FIG. 14B shows that a high Dean number results in remixing of the sample fluid which, in-turn, results in defocusing of the core flow.
Figure 15A:
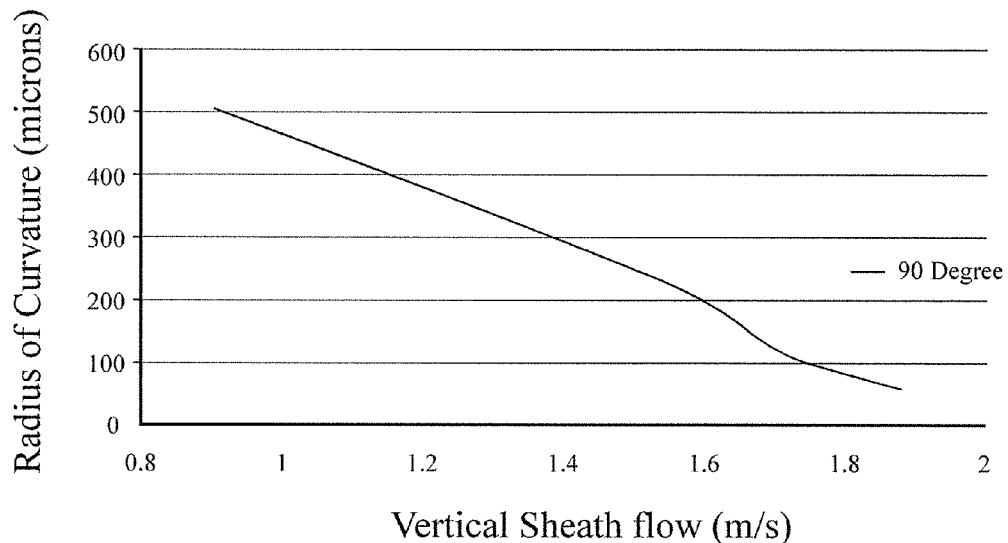
FIGS. 15A-D are design graphs for flow cytometry devices based upon radius of curvature versus sheath flow for 90°, 135°, 180° and 235° curvature lengths, respectively.
Figure 15B:
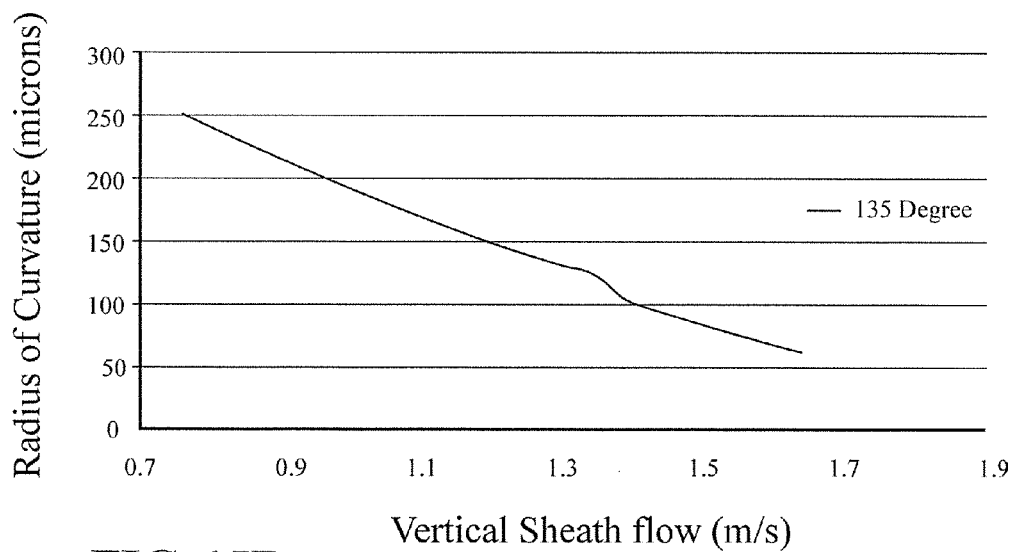
Figure 15C:
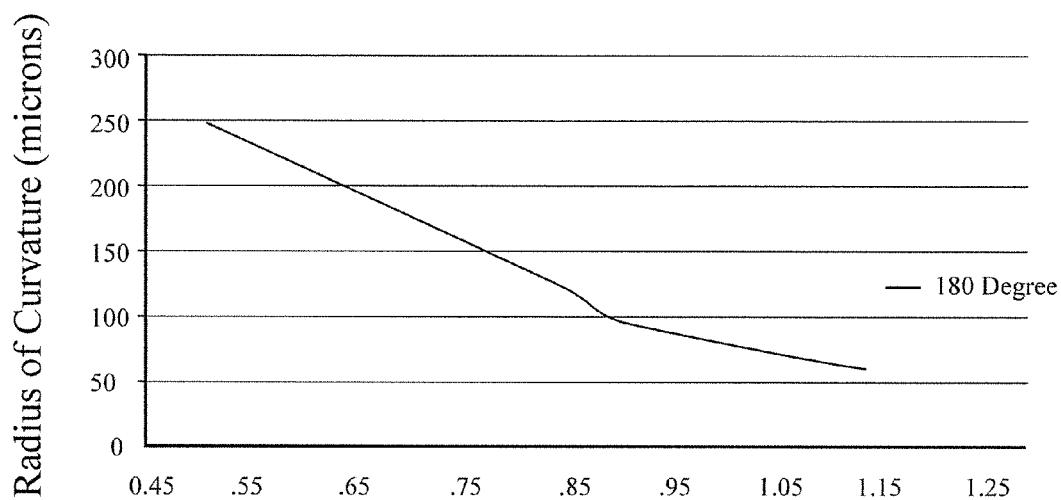
Figure 15D:
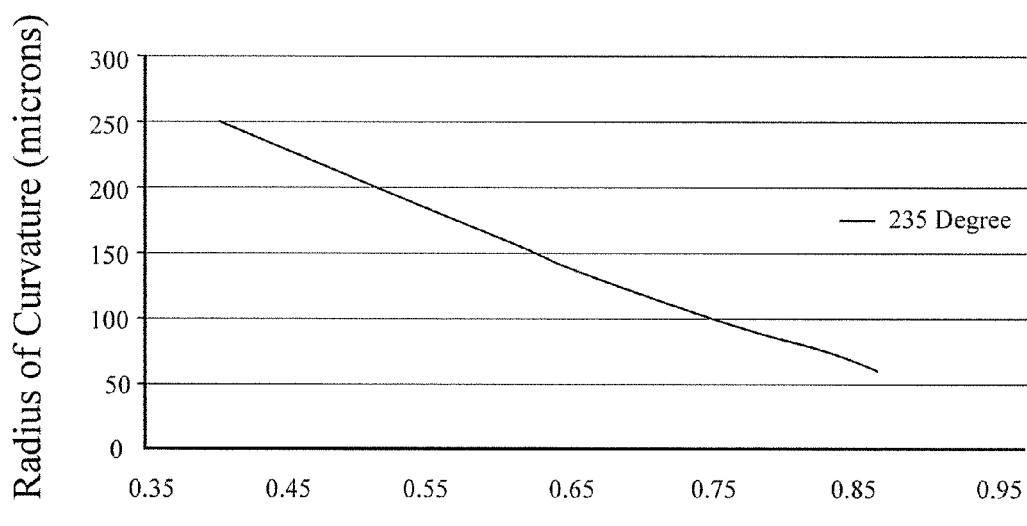

FIG. 14A shows ideal focusing counterflows, and FIG. 14B shows remixing of the sample fluid which occurs due to the higher velocity of the counter-rotating vortices.

FIGS. 15A-D provide guidelines for focusing design. For curvature lengths greater than 235°, it is recommended to use an aspect ratio of greater than 4:3. This gives more space in the channel cross-section for the counter-rotating vortices to achieve vertical focusing more effectively, without causing remixing of the sample fluid which can occur due to the higher velocity of the counter-rotating vortices (shown in FIG. 14B). An improved method of designing the curved channel includes selecting a curve segment angle (or bend angle of the curved channel), a radius of curvature, and then selecting the vertical sheath flow to give optimized particle focusing the guidelines provided.

Figure 16:
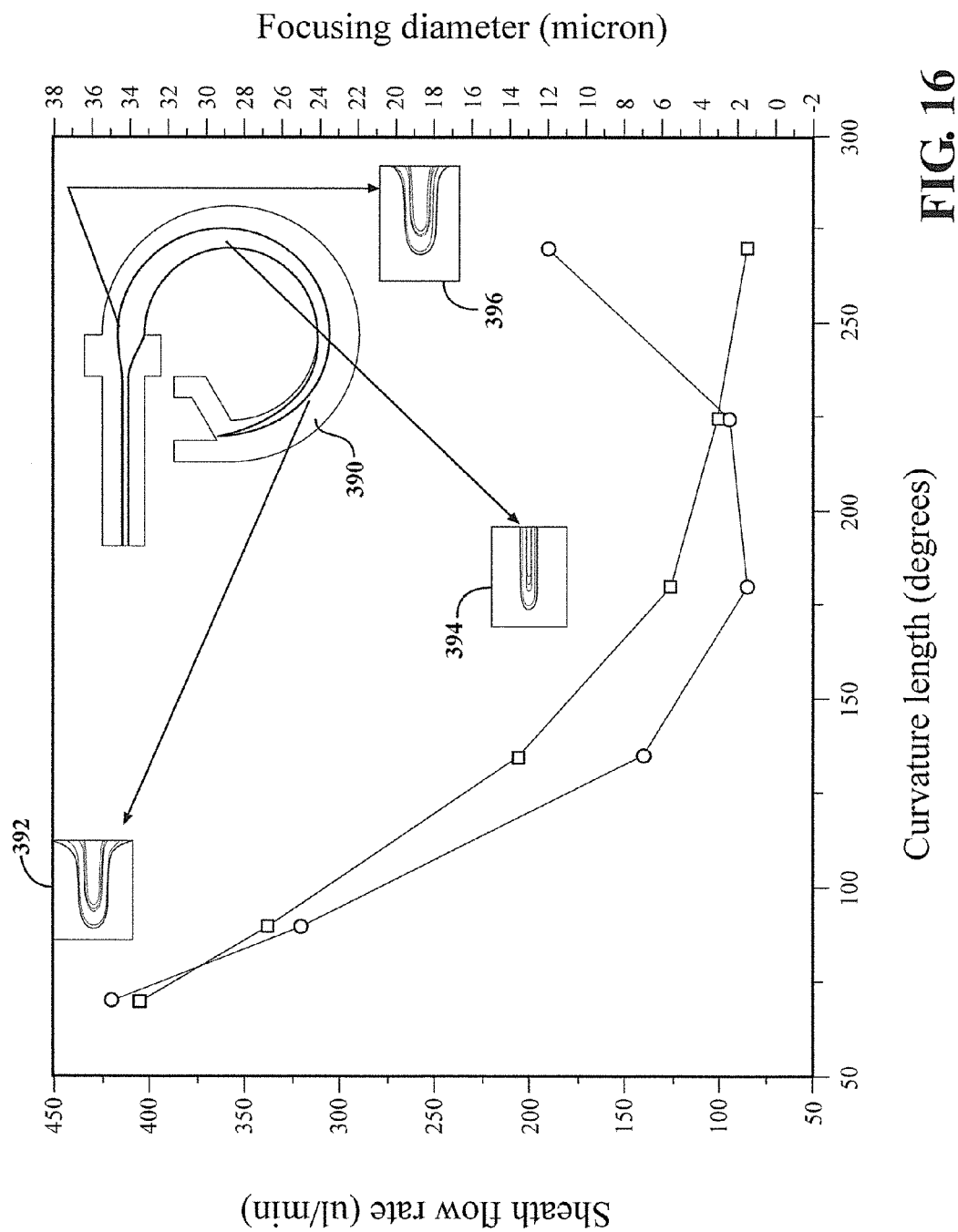
FIG. 16 shows sheath flow and focusing diameter as a function of curvature length (the curved channel bend angle).

FIG. 16 shows that the vertical sheath flow (the left y-axis and the x-axis) keeps decreasing with decrease in the curvature angle. This is because of the decrease in the vertical sheath flow necessary to prevent remixing in the channel. The data shows that the minimum focusing diameter is achieved near 180 degrees, and for higher angles the focusing diameter starts to increase again, because of the decrease in the velocity of counter rotating vortices which result due to decrease in the vertical sheath fluid. Focusing diameter is shown on the right y-axis and the x-axis, for optimized sheath fluid for focusing at a particular curvature angle. All the results were optimized for best possible focusing width. The figure also shows flow profiles 392, 394, and 396 at various positions around the curved channel 390.

A curved channel angle of around 180° can give remarkably low focusing diameters, allowing micron-scale particles to be focused and characterized. Curve angles of between 135° and 225° give remarkably good results, particularly when compared with 90° data.

Examples of the present invention include apparatus such as a portable fluorescence-activated cell-sorting device, providing a similar focusing resolution as commercial flow cytometry devices, but with much lower total flow rate to achieve the desired results. Example portable devices may be used in research, medical clinics, and can be used as excellent disease diagnostic devices for patients that are far from hospitals, including battlefield and disaster area medical applications.

Moreover, examples of the present invention include devices that are much cheaper to fabricate, compared to the present commercial flow cytometry devices. Thus, for underdeveloped countries, this can be an extremely useful clinical tool which may quickly become an efficient and cost-effective lifesaver.

Advantages over the existing commercial flow cytometry device include: focusing width suitable for detection of microorganisms as small as bacteria; a much lower sheath flow, contributing to at least a 50% reduction in running costs as compared to a commercial flow cytometry device; capability of being integrated into a portable setup; design guidelines provided herein for designing a new device based upon required design parameters; conveniently integration with other lab-on-a-chip components, such as ultrasonic cell sorters; and a high throughput capable of competing with any commercially available flow cytometry device Improvement in focusing width by increasing curvature of the channel has a twofold benefit of decrease in vertical sheath flow, which is exactly the opposite as in the case of any commercial flow cytometry device.

Examples of the present invention include a microfluidic-based, fluorescence-activated, cell sorting device, which is an extremely powerful, high throughput, single cell analysis device that can be used for diagnosing many life threatening diseases such as HIV, detection of cancerous tumor cells, and the like.

In other examples, the designed microfluidic chip can be integrated with on-chip optical fibers so as to develop a fully integrated device capable of detecting microorganisms as small as bacteria, which is in the order of 1 micron.

Example devices may be integrates with a cell sorting mechanism, such as a SAW-based sorting mechanism. Example devices may include a feedback control mechanism, allowing for the sorting of desired cells or particles from a group, based on optically scattered signals.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims.

Having described our invention, we claim:

1. An apparatus, the apparatus being a planar microfluidic device, the apparatus comprising:
   a substrate;
   a sample flow inlet, configured to receive a sample flow;
   a first flow inlet, configured to receive a first sheath flow;
   a curved channel, the curved channel configured to receive the sample flow adjacent to the first sheath flow,
   the sample flow inlet, the first flow inlet, and the curved channel being supported by the substrate,
   the curved channel having a bend angle,
   the curved channel being configured to provide vertical hydrodynamic focusing of the sample flow when the sample flow and first sheath flow pass together through the curved channel,
   the sample flow being compressed along a direction normal to the substrate to form a horizontal sample flow sandwiched between split vertical focusing sheath flows;
   at least one inlet for an in-plane hydrodynamic focusing sheath flow; and
   an output channel, receiving the sample flow, the first sheath flow, and the in-plane hydrodynamic focusing sheath flow,
   the first sheath flow and the in-plane hydrodynamic focusing sheath flow together providing three-dimensional hydrodynamic focusing of the sample flow within the output channel,
   the sample flow, the first sheath flow, and the in-plane hydrodynamic focusing sheath flows being co-planar.

2. The apparatus of claim 1, further including a laser configured to excite the sample flow within the output channel.

3. The apparatus of claim 2, further including a radiation detector configured to receive radiation from the sample flow, the radiation being induced by the laser.

4. The apparatus of claim 1, the curved channel having a bend angle of between 135 degrees and 225 degrees, inclusive.

5. The apparatus of claim 1, the curved channel having a bend angle of approximately 180 degrees.

6. The apparatus of claim 1, said in-plane hydrodynamic focusing sheath flow horizontally crossing the direction of said sample flow.

7. The apparatus of claim 1, said in-plane hydrodynamic focusing sheath flow intersecting said sample flow downstream from said curved channel.

8. An apparatus, the apparatus being a planar microfluidic device configured to receive a sample flow, a first sheath flow, and an in-plane hydrodynamic focusing sheath flow, the apparatus comprising:
- a substrate;
- a sample flow inlet configured to receive the sample flow;
- a first sheath inlet configured to receive the first sheath flow;
- the sample flow inlet being configured adjacent to the first sheath flow inlet;
- a curved channel supported by and generally parallel to the substrate,
   - the sample flow inlet and first sheath inlet being configured to deliver the sample flow and the first sheath flow to the curved channel,
   - the curved channel being configured to provide hydrodynamic focusing of the sample flow, the sample flow being compressed in a direction normal to the substrate to form a horizontal sample flow sandwiched between split vertical focusing sheath flows;
- at least one inlet configured to receive the in-plane focusing sheath flow;
- an output channel, the first sheath flow and the in-plane hydrodynamic focusing sheath flow together providing three-dimensional hydrodynamic focusing of the sample flow within the output channel;
- an excitation source configured to excite the sample flow at an excitation point within the output channel; and
- a radiation detector configured to receive detected radiation from the excitation point.

9. The apparatus of claim 8, the excitation source being a laser, laser radiation being conveyed to the output channel by an optical path including an optical fiber.

10. The apparatus of claim 8, the detected radiation including fluorescence.

11. The apparatus of claim 8, the detected radiation being scattered radiation.

12. The apparatus of claim 8, further comprising a first optical fiber configured to convey radiation from excitation source to the excitation point, and a second optical fiber configured to collect radiation from the excitation point.

13. The apparatus of claim 8, the apparatus being a single-layer planar microfluidic flow cytometer.

14. The apparatus of claim 8, the curved channel having a bend angle at least 135 degrees.

15. The apparatus of claim 8, the curved channel having a bend angle of at least 180 degrees.

16. The apparatus of claim 8, the curved channel having a bend angle between 135 degrees and 225 degrees.

17. The apparatus of claim 8, the sample flow having a focus width at the excitation point, the focus width being less than 10 microns.

18. A method of hydrofluidic focusing a sample flow in a planar microfluidic device having a planar substrate, the sample flow being a fluidic suspension of particles, the method comprising:
- passing the sample flow and an adjacent sheath flow through a curved channel section disposed on the planar substrate to induce horizontal drifting of said sample flow to form a horizontal sample flow sandwiched between split vertical focusing sheath flows, the curved channel section providing hydrofluidic focusing of the sample flow in a direction generally normal to the planar substrate;
- passing the sample flow through a linear channel section between a pair of in-plane focusing sheath flows so as to obtain three-dimensional hydrofluidic focusing of the sample flow within an output channel,
- the sample flow, the sheath flow, and the pair of in-plane focusing sheath flows being generally coplanar; and
- characterizing the particles within the output channel.

19. The method of claim 18, the sample flow including biological cells,
- the method including hydrodynamic focusing of the biological cells within the sample flow to allow characterization of the biological cells.

20. The method of claim 18, the sample flow including fluorescent molecules,
- the method including hydrodynamic focusing of the fluorescent molecules to facilitate detection of the fluorescent molecules using single-molecule fluorescence spectroscopy.

* * * * *